United States Patent [19]
Ejima et al.

[11] Patent Number: 5,852,019
[45] Date of Patent: Dec. 22, 1998

[54] PYRIMIDINYLPYRAZOLE DERIVATIVES

[75] Inventors: Akio Ejima; Masamichi Sugimori; Ikuo Mitsui, all of Tokyo, Japan

[73] Assignee: Daiichi Pharmaceutical Co., Ltd., Tokyo, Japan

[21] Appl. No.: 821,076

[22] PCT Filed: Sep. 25, 1995

[86] PCT No.: PCT/JP95/01934

§ 371 Date: Feb. 4, 1998

§ 102(e) Date: Feb. 4, 1998

[87] PCT Pub. No.: WO96/10024

PCT Pub. Date: Apr. 4, 1996

[30] Foreign Application Priority Data

Sep. 26, 1994 [JP] Japan ................................. 6-229422
Jun. 1, 1995 [JP] Japan ................................. 7-135010

[51] Int. Cl.$^6$ ...................... A61K 31/495; C07D 401/14; C07D 403/14; C07D 413/14
[52] U.S. Cl. ..................... 514/252; 514/235.8; 514/273; 544/122; 544/123; 544/238; 544/295; 544/296; 544/321; 544/324; 544/331
[58] Field of Search ..................... 544/122, 123, 544/238, 295, 296, 321, 324, 331; 514/235.8, 252, 273

[56] References Cited

U.S. PATENT DOCUMENTS 5,102,893  4/1992  Picard et al. ................ 514/313

FOREIGN PATENT DOCUMENTS 20938503A  2/1971  Germany .
48-42072   12/1973  Japan .
61129129A  6/1996  Japan .

OTHER PUBLICATIONS

Ubusawa et al., "1–(4–Methoxy–6–methyl–2–pyrimidinyl)–3–methyl–5–methtoxypyrazole and related compunds as neoplasm inhibitors", *Chemical Abstr.*, abstr. No. 183956, 105:21, Nov. 24, 1986.

Ueno et al., "Pyrazole derivatives", *Chemical Abstr.,* abstr. No. 3933q, 81:1:, Jul. 8, 1974.

*Primary Examiner*—Emily Bernhardt
*Attorney, Agent, or Firm*—Sughrue, Mion, Zinn, Macpeak & Seas, PLLC

[57] ABSTRACT

The present invention provides a novel compound which is represented by formula (I):

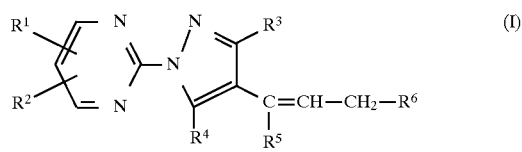

wherein preferable examples of $R^1$ to $R^6$ are as follows; $R^1$ and $R^2$ are each an alkyl group optionally substituted by a halogen atom, an amino group, a hydroxyl group, an alkoxyl group or a thiol group, a hydrogen atom, a halogen atom or an alkoxyl group; $R^3$ is a hydrogen atom; $R^4$ is a methyl group; $R^5$ is a hydrogen atom or an alkyl group; and $R^6$ is a group of the formula:

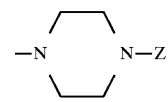

wherein Z is a phenyl group; and has an antitumor effect.

11 Claims, No Drawings

PYRIMIDINYLPYRAZOLE DERIVATIVES

TECHNICAL FIELD

This invention relates to novel compounds having antitumor effects, antitumor agents containing these compounds as an active ingredient and a method for treating tumors with the use of these antitumor agents.

BACKGROUND ART

It has been known that pyrimidinylpyrazole derivatives have hypotensive and psychotropic effects (see, for example, JP-B-47-14233 and JP-B-48-42072; the term "JP-B" as used herein means an "examined Japanese patent publication"). However no antitumor effect of these compounds has been reported so far.

An object of the present invention is to provide highly efficacious antitumor agents having novel chemical structures which have never been known hitherto.

DISCLOSURE OF THE INVENTION

As the results of extensive studies, the present inventors have found out that a novel pyrimidinylpyrazole derivative represented by the following formula (I) has a potent antitumor effect, thus completing the present invention.

The present invention relates to a compound represented by formula (I):

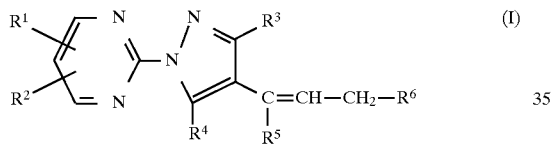

wherein $R^1$ and $R^2$ may be either the same or different and each represents an atom or a substituent selected from a group consisting of:

(1) a hydrogen atom,
(2) a halogen atom,
(3) an amino group,
(4) an alkylamino group,
(5) a dialkylamino group,
(6) a hydroxyl group,
(7) a thiol group,
(8) an alkylthio group,
(9) an alkoxyl group,
(10) a cyano group,
(11) a carbamoyl group,
(12) an alkyl group optionally substituted by a halogen atom, an amino group, an alkylamino group, a dialkylamino group, a hydroxyl group, an alkoxyl group or a thiol group, and
(13) an alkenyl group optionally substituted by a halogen atom, an amino group, an alkylamino group, a dialkylamino group, a hydroxyl group, an alkoxyl group or a thiol group;
$R^3$ represents a hydrogen atom or an alkyl group;
$R^4$ represents a hydrogen atom, an alkyl group, a phenyl group or a benzyl group;
$R^5$ represents a hydrogen atom or an alkyl group; and
$R^6$ represents a tetrahydroisoquinolyl group,
a morpholinyl group,
a piperidyl group,
a piperazinyl group,

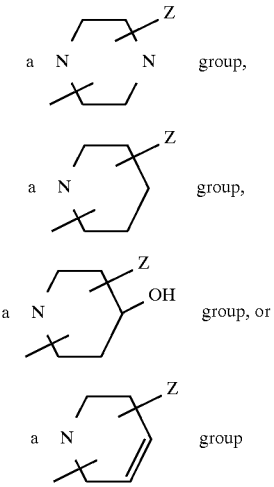

wherein Z represents a phenyl group,
a pyridyl group,
a pyrimidinyl group,
a pyrazinyl group,
a pyridazinyl group,
a piperidyl group,
a benzyl group,
a benzhydryl group,

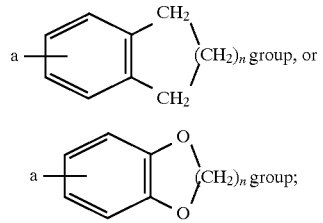

n represents an integer of from 1 to 3; and $R^6$ is optionally substituted by one or more atom(s) and/or substituent (s) selected from a group consisting of:
a halogen atom,
an amino group,
an alkylamino group,
a dialkylamino group,
an acetylamino group,
a nitro group,
a hydroxyl group,
a thiol group,
an alkylthio group,
an alkoxyl group,
a cyano group,
a carbamoyl group,
an alkyl group optionally substituted by a halogen atom, an amino group, an alkylamino group, a dialkylamino group, a hydroxyl group, an alkoxyl group or a thiol group, and
an alkenyl group optionally substituted by a halogen atom, an amino group, an alkylamino group, a dialkylamino group, a hydroxyl group, an alkoxyl group or a thiol group; its salt, and an antitumor agent containing the same as an active ingredient.

The compound of the present invention represented by the formula (I) involves compounds having a double bond of cis-form in the alkenyl group as well as those having a double bond of trans-form therein.

MODE FOR CARRYING OUT THE INVENTION

Now, the substituents as used herein will be described.

The term "alkyl" employed for the alkyl moieties of the alkylamino, dialkylamino, alkylthio and alkoxyl groups and the alkyl group herein means an alkyl group having from 1 to 6 carbon atoms.

Preferable examples of $R^1$ and $R^2$ include:

an alkyl group optionally substituted by a halogen atom, an amino group, a hydroxyl group, an alkoxyl group or a thiol group, a hydrogen atom, a halogen atom, an alkylamino group, a dialkylamino group, an alkoxyl group, a cyano group, and a carbamoyl group.

It is still preferable that $R^1$ and $R^2$ are selected from a group consisting of an alkyl group optionally substituted by a halogen atom, an amino group, a hydroxyl group, an alkoxyl group or a thiol group, a halogen atom, a hydrogen atom and an alkoxyl group.

It is preferable that $R^3$ is a hydrogen atom.

It is preferable that $R^4$ is a hydrogen atom or an alkyl group, still preferably a methyl group.

It is preferable that $R^5$ is a hydrogen atom or an alkyl group, still preferably a hydrogen atom or a methyl group.

It is preferable that $R^6$ represents

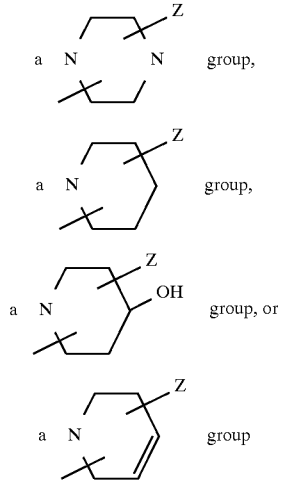

wherein Z is as defined above;
each optionally substituted by one or more substituents selected from a group consisting of:

an alkyl group optionally substituted by a halogen atom, an amino group, a hydroxyl group, an alkoxyl group or a thiol group, a halogen atom, an alkylamino group, a dialkylamino group, an alkoxyl group, a cyano group, a hydroxyl group, and a carbamoyl group.

It is preferable that the substituent, which is selected from a group consisting of an alkyl group optionally substituted by a halogen atom, an amino group, a hydroxyl group, an alkoxyl group or a thiol group, a halogen atom, an alkylamino group, a dialkylamino group, an alkoxyl group, a cyano group, a hydroxyl group and a carbamoyl group, is attached to the Z moiety. It is still preferable that $R^6$ represents

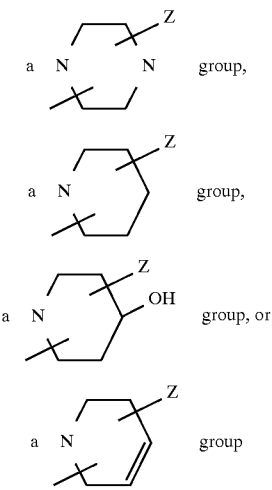

each optionally substituted by one or more substituents selected from a group consisting of an alkyl group optionally substituted by a halogen atom, an amino group or a hydroxyl group, a halogen atom, a hydroxyl group and an alkoxyl group.

It is preferable that the substituent, which is selected from a group consisting of an alkyl group optionally substituted by a halogen atom, a halogen atom and an alkoxyl group, is attached to the Z moiety.

A particularly preferred example of $R^6$ is a group

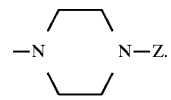

It is preferable that Z represents a phenyl group, a pyridyl group, a pyrimidinyl group, a pyrazinyl group, a pyridazinyl group and a piperidyl group. It is still preferable that Z is a phenyl group. When this phenyl group has substituent(s), it is preferable that the substituent(s) are located at the o- and/or m-positions regarding the binding site of the heterocyclic ring.

The compound (I) of the present invention can be produced by various methods. Typical examples of the production methods thereof are as follows.

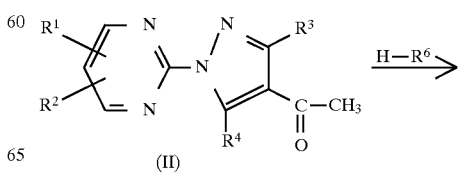

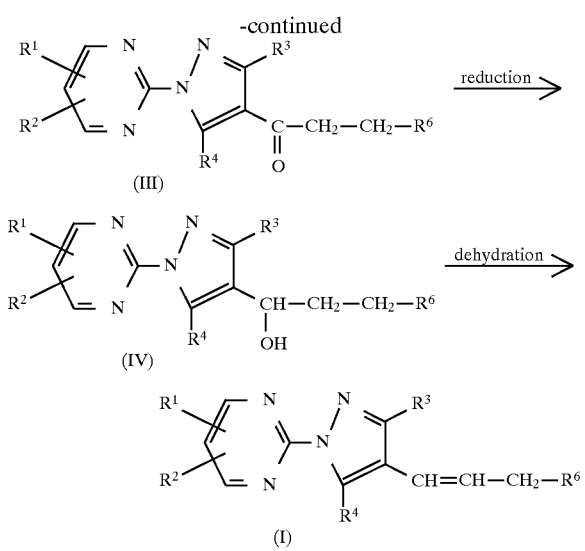

wherein $R^1$, $R^2$, $R^3$, $R^4$ and $R^6$ are each as defined above.

Namely, the compound (II) is subjected to a Mannich reaction with a basic compound H—$R^6$. The compound (III) thus obtained is then converted into the compound (IV) by reduction and then dehydrated. Thus the target compound (I) can be obtained.

Now, each reaction will be described in greater detail.

Mannich Reaction

In the presence of a condensation agent, the compound (II) and the basic compound H—$R^6$ are treated in a solvent to thereby give the compound (III). It is recommended to use H—$R^6$ in the form of a salt such as hydrochloride or hydrobromide.

Examples of the solvent usable herein include alcohol solvents such as methanol, ethanol and propanol, amide solvents such as N,N-dimethylformamide, acetamide and dimethylacetamide, halogenated hydrocarbon solvent such as chloroform, dichloromethane and carbon tetrachloride, ether solvents such as diethyl ether, tetrahydrofuran and dioxane, and aromatic hydrocarbon solvents such as benzene, toluene and xylene. It is also possible to use a mixture of these solvents.

Examples of the condensation agent include paraformaldehyde and formaldehyde.

The reaction temperature usually ranges from -20° to 150° C., preferably from 0° to 100° C.

The reaction time usually ranges from 5 minutes to 120 minutes, preferably from 30 minutes to 72 hours.

Reduction

The compound (III) is reduced in a solvent to thereby give the corresponding compound (IV).

Examples of the solvent usable herein include alcohol solvents such as methanol, ethanol and propanol, amide solvents such as N,N-dimethylformamide, acetamide and dimethylacetamide, halogenated hydrocarbon solvent such as chloroform, dichloromethane and carbon tetrachloride, ether solvents such as diethyl ether, tetrahydrofuran and dioxane, and aromatic hydrocarbon solvents such as benzene, toluene and xylene. It is also possible to use a mixture of these solvents.

The reduction may be performed by a method commonly employed in the art. For example, the compound (III) may be treated in the presence of a reducing agent or hydrogenated in the presence of a catalyst.

Examples of the reducing agent include boron hydride compounds and aluminum hydride compounds such as sodium boron hydride, sodium cyanoboron hydride and lithium aluminum hydride. Examples of the catalyst include palladium, Raney nickel and platinum oxide.

The reaction temperature usually ranges from -20° to 150° C., preferably from 0° to 100° C.

The reaction time usually ranges from 5 minutes to 72 hours, preferably from 10 minutes to 24 hours.

Dehydration

The compound (IV) is dehydrated in a solvent to thereby give the target compound (I).

Examples of the solvent usable herein include alcohol solvents such as methanol, ethanol and propanol, amide solvents such as N,N-dimethylformamide, acetamide and dimethylacetamide, halogenated hydrocarbon solvent such as chloroform, dichloromethane and carbon tetrachloride, ether solvents such as diethyl ether, tetrahydrofuran and dioxane, and aromatic hydrocarbon solvents such as benzene, toluene and xylene. It is also possible to use a mixture of these solvents.

The dehydration may be performed by a method commonly employed in the art. For example, the compound (IV) may be heated in the presence of an acid.

As the acid, use can be made of either an organic acid or an inorganic acid. Examples of the inorganic acid include hydrochloric acid, sulfuric acid, hydrobromic acid and potassium hydrogensulfate, while examples of the organic acid include p-toluenesulfonic acid, methaneslufonic acid and oxalic acid. An inorganic acid is preferable as the acid. Alternatively, alumina is usable therefor.

The reaction temperature usually ranges from -20° to 150° C., preferably from 0° to 100° C.

The reaction time usually ranges from 5 minutes to 72 hours, preferably from 10 minutes to 24 hours.

By the above-mentioned synthesis method, a compound, wherein $R^5$ is a hydrogen atom and the alkenyl moiety is in the trans-form, can be obtained. On the other hand, a compound wherein $R^5$ is an alkyl group or the alkenyl moiety is in the cis-form can be synthesized by the following method.

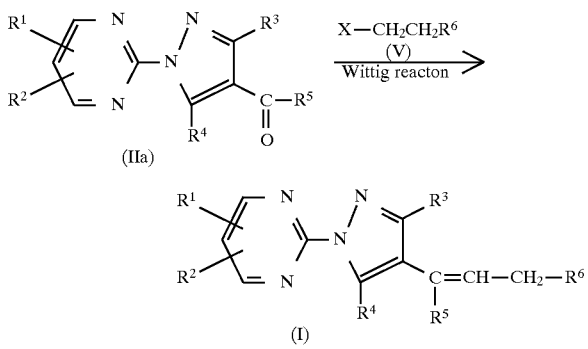

wherein X represents a chlorine atom, a bromine atom or an iodine atom; and $R^1$, $R^2$, $R^3$, $R^4$, $R^5$ and $R^6$ are each as defined above;

Namely, the compound (IIa) is subjected to a Wittig reaction with the compound (V) to thereby give the compound represented by the formula (I).

Now, this production method will be described in greater detail.

The compound (V) is reacted with a tertiary phosphine. in a solvent. The phosphonium salt thus obtained is treated with a base in a solvent and then reacted with the compound (IIa) to thereby give the compound (I).

Examples of the solvent usable herein include ether solvents such as diethyl ether, tetrahydrofuran and dioxane, aromatic hydrocarbon solvents such as benzene, toluene and xylene, alcohol solvent such as methanol, ethanol and propanol, amide solvents such as N,N-dimethylformamide, acetamide and dimethylacetamide, and halogenated hydrocarbon solvents such as chloroform, dichloromethane and carbon tetrachloride. It is also possible to use a mixture of these solvents.

Examples of the tertiary phosphine to be used herein include triphenylphosphine and tri-n-butylphosphine.

Examples of the base include n-butyllithium, phenyllithium, sodium hydride, t-butoxypotassium, sodium ethoxide and 1,8-diazabicyclo[5.4.0]undec-7-ene (DBU).

The reaction temperature usually ranges from 30° to 150° C., preferably from 50° to 100° C.

The reaction time usually ranges from 5 minutes to 72 hours, preferably from 10 minutes to 24 hours.

The starting compounds, namely, the compounds (II) and (IIa) and the basic compounds H—$R^6$ and X—$CH_2CH_2R^6$ are each either a publicly known compound or one which can be easily synthesized by a publicly known method.

The compound of the present invention may be converted into a physiologically acceptable salt thereof with an inorganic acid such as hydrochloric acid, sulfuric acid or phosphoric acid or an organic acid such as formic acid, acetic acid or methanesulfonic acid, if desired.

BEST MODE FOR CARRYING OUT THE INVENTION

The following Experimental Examples will show the antitumor effects of the compounds of the present invention obtained by the above-mentioned methods.

Experimental Example 1

Two tumor cell lines P388 and PC-6, which had been subcultured in a medium RPMI1640 containing 10% of fetal calf serum, 2 mM of L-glutamine and 100 µg/ml of kanamycin sulfate, were respectively inoculated into 96-well microplates at cell densities of $5.0\times10^2$ cell/150 µl/well (P388) and $5.0\times10^3$ cell/150 µl/well (PC-6). After 2 hours (P388) and 24 hours (PC-6), 50 µl/well portions of a specimen were added. After incubating for 3 days, a 5 mg/ml solution of MTT [3-(4,5-dimethylthiazol-2-yl)-2,5-diphenyl-2H-tetrazolium bromide] was added thereto at a ratio of 20 µl/well. Four hours thereafter, the culture medium was eliminated and dimethylsulfoxide was added at a ratio of 150 µl/well. Then the absorbance was measured at 540 nm. The antitumor effect was expressed in the concentration (µg/ml) of the drug at which the growth of the cell of the test group was suppressed by 50% based on-that of the control group ($GI_{50}$).

TABLE 1

| Compound | P388 (µg/ml) | PC-6 (µg/ml) |
|---|---|---|
| Ex. 1 | 0.029 | 0.019 |
| Ex. 2 | 0.349 | 0.131 |
| Ex. 3 | 0.614 | 0.194 |
| Ex. 5 | 0.087 | 0.035 |
| Ex. 7 | 0.052 | 0.046 |
| Ex. 12 | 0.410 | 0.179 |
| Ex. 15 | 0.245 | 0.057 |
| Ex. 17 | 0.117 | 0.027 |
| Ex. 18 | 0.586 | 1.140 |
| Ex. 20 | 0.165 | 0.073 |
| Ex. 21 | 0.520 | 0.608 |
| Ex. 23 | 1.252 | 0.409 |
| Ex. 25 | 0.135 | 0.069 |

TABLE 1-continued

| Compound | P388 (µg/ml) | PC-6 (µg/ml) |
|---|---|---|
| Ex. 27 | 0.009 | 0.005 |
| Ex. 28 | 0.014 | 0.006 |

Experimental Example 2

P388 mouse leukemic cells were intraperitoneally transplanted into CDF-1 male mice aged 7 to 10 weeks (body weight: 21–34 g, each group having 6 animals) at a ratio of $1\times10^6$ cells per animal. A test substance was intraperitoneally administered to the animals 1 day and 5 days after the transplantation and the life-prolongation effect was observed.

The test substance was dissolved or suspended in a BTC solution (a solution of 0.9% of benzyl alcohol, 0.4% of Tween 80 and 0.5% of sodium carboxymethylcellulose dissolved in distilled water for injection) prior to the administration.

The antitumor effect was expressed in [T/C×100] wherein T stands for the median of the survival time (days) of the test group and C stands for that of the control group to which no test substance had been given.

TABLE 2

| Compound | Total dose (mg/kg) | T/C (%) |
|---|---|---|
| Ex. 1 | 77 × 2 | 169 |
|  | 61 × 2 | 157 |
| Ex. 5 | 163 × 2 | 147 |
|  | 112 × 2 | 138 |
|  | 78 × 2 | 126 |
| Ex. 7 | 100 × 2 | 138 |
|  | 80 × 2 | 132 |
|  | 64 × 2 | 131 |
| Ex. 15 | 200 × 2 | 154 |
|  | 140 × 2 | 140 |
| Ex. 27 | 200 × 2 | 148 |
|  | 100 × 2 | 133 |

As Tables 1 and 2 clearly show, the compounds synthesized in the present invention have antitumor activities and thus can be used as antitumor agents in the treatment of various tumors.

The antitumor agent of the present invention can be administered by various method, for example, in the form of various injections such as intravenous injection, intramuscular injection or hypodermic injection or oral preparations. Among these administration routes, intravenous injection in the form of an aqueous preparation and oral administration are particularly preferable.

An aqueous preparation can be formed by converting the compound of the present invention into an acid addition salt with the use of a pharmacologically acceptable acid or an alkali metal salt such as sodium salt.

In the case of oral administration, the compound of the present invention may be in the form of either a free compound or a salt.

These preparations may be produced by selecting an appropriate form depending on the administration route and using various methods commonly employed in the art.

Examples of the oral preparations suitable for the antitumor agent of the present invention include tablets, dusts, granules, capsules, solutions, syrups, elixirs and oily or aqueous suspensions.

An injection may further contain stabilizers, preservatives and dissolution aids. Also, a solution, which optionally contains these adjuvants, may be packed into a container and solidified by, for example, freeze-drying to thereby give a product to be prepared before using. Each container may have the preparation in a single dose. Alternatively, the preparation may be packed in a container in an amount corresponding to two or more doses.

Examples of a liquid preparation include solutions, suspensions and emulsions. To produce these preparations, use can be further made of additives such as suspending agents and emulsifiers.

The antitumor agent containing the compound of the present invention is administered to an adult in an appropriate dose (in terms of the compound) once a day. It is preferable to repeatedly administer the antitumor agent at appropriate intervals. The dose ranges from 10 mg to 3 g, preferably from 50 mg to 2 g.

EXAMPLES

To further illustrate the present invention in greater detail, the following Examples will be given.

Example 1
1-[5-Methyl-1-(2-pyrimidinyl)-4-pyrazolyl]-3-[4-(3-chlorophenyl)-1-piperazinyl]-1-trans-propene hydrochloride 10 g of 1-[5-methyl-1-(2-pyrimidinyl)-4-pyrazolyl]-3-[4-(3-chlorophenyl)-1-piperazinyl]-1-propanone hydrochloride was dissolved in a solvent mixture comprising 600 ml of tetrahydrofuran and 600 ml of ethanol. After cooling to 0° C., 2.5 g of sodium boron hydride was added thereto and the resulting mixture was stirred at the same temperature for 45 minutes. To the reaction mixture was further added 500 mg of sodium boron hydride followed by stirring for 1 hour. After adding 30 ml of 4N hydrochloric acid to the reaction mixture, the solvent was distilled off. To the residue thus obtained were added 1,200 ml of tetrahydrofuran and 5.9 g of p-toluenesulfonic acid monohydrate. Then the mixture was heated under reflux for 2 hours. After evaporating the solvent, it was neutralized with an aqueous solution of sodium hydroxide and extracted with ethyl acetate. The extract was washed with a saturated aqueous solution of sodium chloride and dried over anhydrous sodium sulfate. After evaporating the solvent, the residue was dissolved in ethyl acetate. Then 22 ml of a 1N hydrochloric acid/ethanol solution was added thereto. The insoluble matters were collected by filtration and recrystallized from ethanol. Thus 4.0 g of the title compound was obtained.

m.p.: 186°–191° C. (decomp.); NMR (in DSMO-$d_6$) δ: 2.62 (s, 3H), 3.0–3.3 (m, 4H), 3.5–3.6 (m, 2H), 3.8–4.0 (m, 4H), 6.23 (dt, 1H, J=16, 7 Hz), 6.82 (d, 1H, J=16 Hz), 6.87 (dd, 1H, J=8, 2 Hz), 6.96 (dd, 1H, J=8, 2 Hz), 7.05 (t, 1H, J=2 Hz), 7.27 (t, 1H, J=8 Hz), 7.53 (t, 1H, J=5 Hz), 8.10 (s, 1H), 8.92 (d, 2H, J=5 Hz).

Example 2
1-[5-Methyl-1-(2-pyrimidinyl)-4-pyrazolyl]-3-[4-phenyl-1-piperazinyl]-1-trans-propene hydrochloride By using 1.35 g of 1-[5-methyl-1-(2-pyrimidinyl)-4-pyrazolyl]-3-[4-phenyl-1-piperazinyl]-1-propanone hydrochloride, the procedure of Example 1 was repeated. After the completion of the post treatment, 265 mg of the title compound was obtained.

m.p.: 197°–201° C. (decomp.); NMR (in DSMO-$d_6$) δ: 2.62 (s, 3H), 3.0–3.2 (m, 4H), 3.5–3.7 (m, 2H), 3.7–3.9 (m, 2H), 3.9–4.0 (m, 2H), 6.24 (dt, 1H, J=15, 7 Hz), 6.83 (d, 1H, J=15 Hz), 7.01 (d, 2H, J=8 Hz), 7.27 (t, 2H, J=8 Hz), 7.54 (t, 1H, J=4 Hz), 7.87 (t, 1H, J=8 Hz), 8.08 (s, 1H), 8.92 (d, 2H, J=4 Hz).

Example 3
1-[5-Methyl-1-(2-pyrimidinyl)-4-pyrazolyl]-3-[4-(2-methylphenyl)-1-piperazinyl]-1-trans-propene hydrochloride By using 3.61 g of 1-[5-methyl-1-(2-pyrimidinyl)-4-pyrazolyl]-3-[4-(2-methylphenyl)-1-piperazinyl]-1-propanone hydrochloride, the procedure of Example 1 was repeated. After the completion of the post treatment, 998 mg of the title compound was obtained.

m.p.: 210°–216° C. (decomp.); NMR (in DSMO-$d_6$) δ: 2.27 (s, 3H), 2.63 (s, 3H), 3.0–3.1.(m, 2H), 3.1–3.3 (m, 4H), 3.5–3.6 (m, 2H), 3.9–4.0 (m, 2H), 6.23 (dt, 1H, J=16, 7 Hz), 6.84 (d, 1H, J=16 Hz), 7.02 (t, 1H, J=8 Hz), 7.06 (d, 1H, J=8 Hz), 7.19 (t, 1H, J=8 Hz), 7.20 (d, 1H, J=8 Hz), 7.54 (t, 1H, J=5 Hz), 8.10 (s, 1H), 8.92 (d, 2H, J=5 Hz).

Example 4
1-[5-Methyl-1-(2-pyrimidinyl)-4-pyrazolyl]-3-[4-(4-fluorophenyl)-1-piperazinyl]-1-trans-propene hydrochloride By using 1.0 g of 1-[5-methyl-1-(2-pyrimidinyl)-4-pyrazolyl]-3-[4-(4-fluorophenyl)-1-piperazinyl]-1-propanone hydrochloride, the procedure of Example 1 was repeated. After the completion of the post treatment, 230 mg of the title compound was obtained.

m.p.: 205°–215° C. (decomp.); NMR (in DSMO-$d_6$) δ: 2.62 (s, 3H), 3.0–3.3 (m, 4H), 3.5–4.1 (m, 6H), 6.23 (dt, 1H, J=15, 7 Hz), 6.83 (d, 1H, J=15 Hz), 7.0–7.3 (m, 4H), 7.54 (t, 1H, J=5 Hz), 8.09 (s, 1H), 8.93 (d, 2H, J=5 Hz).

Example 5
1-[5-Methyl-1-(2-pyrimidinyl)-4-pyrazolyl]-3-[4-(2-chlorophenyl)-1-piperazinyl]-1-trans-propene hydrochloride 3.7 g of 1-[5-methyl-1-(2-pyrimidinyl)-4-pyrazolyl]-3-[4-(2-chlorophenyl)-1-piperazinyl]-1-propanone hydrochloride was dissolved in 300 ml of methanol. After adding 1.25 g of sodium boron hydride, the obtained mixture was stirred at room temperature for 2 hours. To the reaction mixture was further added 0.6 g of sodium boron hydride followed by stirring for 2 hours. Under ice cooling, water was added to the reaction mixture and the methanol was removed by evaporation. The residue was extracted with chloroform and the extract was washed with a saturated aqueous solution of sodium chloride and dried over anhydrous sodium sulfate. After evaporating the solvent, the residue was subjected to silica gel column chromatography and developed with a solvent mixture (chloroform/methanol, 30:1) to thereby give 1-[5-methyl-1-(2-pyrimidinyl)-4-pyrazolyl]-3-[4-(2-chlorophenyl-)1-piperazinyl]-1-propanol. Next, 16 ml of a 1N hydrochloric acid/ethanol solution was added to the product. After dissolving by heating, ether was further added thereto. The crystals thus precipitated were collected by filtration to thereby give 1.26 g of the title compound.

m.p.: 245°–250° C. (decomp.); NMR (in DSMO-$d_6$) δ: 2.62 (s, 3H), 3.0–3.3 (m, 4H), 3.4–3.7 (m, 4H), 3.9–4.1 (m, 2H), 6.25 (dt, 1H, J=16, 7 Hz), 6.85 (d, 1H, J=16 Hz), 7.1–7.2 (m, 1H), 7.2–7.3 (m, 1H), 7.3–7.5 (m, 211), 7.5–7.6 (m, 1H), 8.08 (s, 1H), 8.92 (d, 2H, J=5 Hz), 11.09 (s, 1H).

Example 6
1-[5-Methyl-1-(2-pyrimidinyl)-4-pyrazolyl]-3- (1,2,3,4-tetrahydroisoquinolin-2-yl)-1-trans-propene hydrochloride
(1) 1-[5-Methyl-1-(2-pyrimidinyl)-4-pyrazolyl]-3-(1,2,3,4-tetrahydroisoquinolin-2-yl)-1-propanone hydrochloride 1.01 g of 1-(2-pyrimidinyl)-4-acetyl-5-methylpyrazole was dissolved in 100 ml of ethanol. After adding 450 mg of paraformaldehyde and 848 mg of 1,2,3,4-tetrahydroisoquinoline hydrochloride, the mixture was heated under reflux overnight. Next, 200 mg of paraformaldehyde was further added to the reaction mixture which was then concentrated by heating under reflux overnight. To the obtained residue was added chloroform. Then it was washed with a saturated aqueous solution of sodium hydrogencarbonate and a saturated aqueous solution of sodium chloride, and dried over anhydrous sodium sulfate. After evaporating the solvent, the residue was subjected to silica gel column chromatography and developed with a solvent mixture (chloroform/methanol, 30:1). A fraction containing the terget compound was concentrated. To the residue thus obtained was added a 1N hydrochloric acid/ethanol solution. After concentration, ethanol was added to the residue. After recrystallization, 550 mg of the title compound was obtained.

m.p.: 165°–168° C. (decomp.); NMR (in DSMO-$d_6$) δ: 2.81 (s, 3H), 3.0–3.9 (m, 8H), 4.3–4.8 (m, 2H), 7.1–7.4 (m, 4H), 7.67 (t, 3H, J=5 Hz), 8.43 (s, 1H), 9.01 (d, 2H, J=5 Hz), 11.09 (s, 1H).

(2) 1-[5-Methyl-1-(2-pyrimidinyl)-4-pyrazolyl]-3-(1,2,3,4-tetrahydroisoquinolin-2-yl)-1-trans-propene hydrochloride 500 mg of the compound obtained in the above (1) was dissolved in a solvent mixture comprising 20 ml of methanol and 40 ml of ethanol. After adding 500 mg of sodium boron hydride, the mixture was stirred at room temperature for 3 hours. Then the reaction mixture was concentrated. After adding chloroform, it was washed with a saturated aqueous solution of sodium chloride and dried over anhydrous sodium sulfate. After evaporating the solvent, 50 ml of tetrahydrofuran, 50 ml of dioxane and 500 mg of p-toluenesulfonic acid monohydrate were added to the residue and the mixture was heated under reflux for 5 hours. After evaporating the solvent, chloroform was added to the residue. Then it was washed with a saturated aqueous solution of sodium hydrogencarbonate and a saturated aqueous solution of sodium chloride, and dried over anhydrous sodium sulfate. After evaporating the solvent, the residue was subjected to silica gel column chromatography and developed with a solvent mixture (chloroform/methanol, 20:1). A fraction containing the terget compound was concentrated. To the residue thus obtained was added a 1N hydrochloric acid/ethanol solution. After concentration, ethanol was added to the residue. After recrystallization, 185 mg of the title compound was obtained.

m.p.: 200°–220° C. (decomp.); NMR (in DSMO-$d_6$) δ: 2.63 (s, 3H), 3.0–4.2 (m, 6H), 4.2–4.7 (m, 2H), 6.29 (dt, 1H, J=15, 7 Hz), 6.87 (d, 1H, J=15 Hz), 7.2–7.4 (m, 4H), 7.54 (t, 1H, J=5 Hz), 8.07 (s, 1H), 8.93 (d, 2H, J=5 Hz).

Example 7

1-[5-Methyl-1-(2-pyrimidinyl)-4-pyrazolyl]-3-[4-(2-fluorophenyl)-1-piperazinyl]-1-trans-propene hydrochloride The procedures of Example 6 (1) and (2) were repeated but substituting the 1,2,3,4-tetrahydroisoquinoline hydrochloride employed in Example 6 (1) by 1-(2-fluorophenyl)piperazine hydrochloride. After the completion of the post treatment, the title compound was obtained.

m.p.: 210°–215° C. (decomp.); NMR (in DSMO-$d_6$) δ: 2.62 (s, 3H), 3.0–3.3 (m, 4H), 3.4–3.7 (m, 4H), 3.9–4.1 (2H, m), 6.24 (dt, 1H, J=15, 7 Hz), 6.84 (d, 1H, J=15 Hz), 7.0–7.3 (m, 4H), 7.54 (t, 1H, J=5 Hz), 8.09 (s, 1H), 8.93 (d, 2H, J=5 Hz).

Example 8

1-[5-Methyl-1-(2-pyrimidinyl)-4-pyrazolyl]-3-[4-methyl-1,2,5,6-tetrahydro-1-pyridyl]-1-trans-propene hydrochloride The procedures of Example 6 (1) and (2) were repeated but substituting the 1,2,3,4-tetrahydroisoquinoline hydrochloride employed in Example 6 (1) by 4-methyl-1,2,5,6-tetrahydropyridine hydrochloride. After the completion of the post treatment, the title compound was obtained.

m.p.: 225°–230° C. (decomp.); NMR (in DSMO-$d_6$) δ: 1.73 (s, 3H), 2.1–2.6 (m, 2H), 2.61 (s, 3H), 3.0–4.0 (m, 8H), 5.43 (s, 1H), 6.20 (dt, 1H, J=15, 7 Hz), 6.81 (d, 1H, J=15 Hz), 7.54 (t, 1H, J=5 Hz), 8.05 (s, 1H), 8.92 (d, 2H, J=5 Hz).

Example 9

1-[5-Methyl-1-(2-pyrimidinyl)-4-pyrazolyl]-3-[4-(4-chlorophenyl)-4-hydroxy-1-piperidyl]-1-trans-propene hydrochloride By using 500 mg of 1-[5-methyl-1-(2-pyrimidinyl)-4-pyrazolyl]-3-[4-(4-chlorophenyl)-4-hydroxy-1-piperidyl]-1-propanone hydrochloride, the procedures of Example 1 was repeated. After the completion of the post treatment, 185 mg of the title compound was obtained.

m.p.: 230°–235° C. (decomp.); NMR (in DSMO-$d_6$) δ: 1.8–2.0 (m, 2H), 2.3–2.5 (m, 2H), 2.62 (s, 3H), 3.2–3.6 (m, 4H), 3.8–4.0 (m, 2H), 5.60 (s, 1H), 6.25 (dt, 1H, J=15, 7 Hz), 6.85 (d, 1H, J=15 Hz), 7.44 (d, 2H, J=8 Hz), 7.49 (d, 2H, J=8 Hz), 7.54 (t, 1H, J=5 Hz), 8.09 (s, 1H), 8.93 (d, 2H, J=5 Hz).

Example 10

1-[5-Methyl-1-(4-methyl-6-methoxy-2-pyrimidinyl)-4-pyrazolyl]-3-[4-(2-methylphenyl)-1-piperazinyl]-1-trans-propene hydrochloride The procedures of Example 6 (1) and (2) were repeated but substituting the 1-(2-pyrimidinyl)-4-acetyl-5-methylpyrazole and 1,2,3,4-tetrahydroisoquinoline hydrochloride employed in Example 6 (1) respectively by 1-(4-methyl-6-methoxy-2-pyrimidinyl)-4-acetyl-5-methylpyrazole and 1-(2-methylphenyl)piperazine hydrochloride. After the completion of the post treatment, the title compound was obtained.

m.p.: 206°–212° C. (decomp.); NMR (in DSMO-$d_6$) δ: 2.27 (s, 3H), 2.45 (s, 3H), 2.66 (s, 3H), 3.0–3.3 (m, 6H), 3.5–3.6 (m, 2H), 3.98 (s, 3H), 3.9–4.0 (m, 2H), 6.24 (dt, 1H, J=16, 8 Hz), 6.81 (s, 1H), 6.84 (d, 1H, J=16 Hz), 7.02 (t, 1H, J=7 Hz), 7.05 (d, 1H, J=7 Hz), 7.19 (d, 1H, J=7 Hz), 7.19 (t, 1H, J=7 Hz), 8.05 (s, 1H).

Example 11

1-[5-Methyl-1-(2-pyrimidinyl)-4-pyrazolyl]-3-[4-(3-chloro-2-methylphenyl)-1-piperazinyl]-1-trans-propene hydrochloride The procedures of Example 6 (1) and (2) were repeated but substituting the 1,2,3,4-tetrahydroisoquinoline hydrochloride employed in Example 6 (1) by 680 mg of 1-(2-chloro-3-methylphenyl)piperazine hydrochloride. After the completion of the post treatment, 93 mg of the title compound was obtained.

m.p.: 210°–218° C. (decomp.); NMR (in DSMO-$d_6$) δ: 2.32 (s, 3H), 2.65 (s, 2H), 3.0–3.2 (m, 2H), 3.2–3.3 (m, 4H), 3.5–3.6 (m, 2H), 3.9–4.0 (m, 2H), 6.24 (dt, 1H, J=16, 8 Hz), 6.84 (d, 1H, J=16 Hz), 7.07 (dd, 1H, J=7, 2 Hz), 7.19 (dd, 1H, J=7, 2 Hz), 7.21 (t, 1H, J=7 Hz), 7.52 (t, 1H, J=5 Hz), 8.07 (s, 1H), 8.91 (d, 2H, J=5 Hz).

Example 12

1-[5-Methyl-1-(4-methyl-2-pyrimidinyl)-4-pryrazolyl]-3-[4-(2-chlorophenyl)-1-piperazinyl]-1-trans-propene hydrochloride The procedures of Example 6 (1) and (2) were repeated but substituting the 1-(2-pyrimidinyl)-4-acetyl-5-methylpyrazole and the 1,2,3,4-tetrahydroisoquinoline hydrochloride employed in Example 6 (1) respectively by 1-(4-methyl-2-pyrimidinyl)-4-acetyl-5-methylpyrazole and 1-(2-chlorophenyl)piperazine hydrochloride. After the completion of the post treatment, the title compound was obtained.

m.p.: 200°–205° C. (decomp.); NMR (in DSMO-$d_6$) δ: 2.55 (s, 3H), 2.61 (s, 3H), 3.1–3.3 (m, 3H), 3.3–3.7 (m, 4H), 3.8–4.0 (m, 2H), 6.26 (dt, 1H, J=16, 8 Hz), 6.84 (d, 1H, J=16 Hz), 7.12 (t, 1H, J=8 Hz), 7.23 (d, 1H, J=8 Hz), 7.3–7.6 (m, 3H), 8.04 (s, 1H), 8.75 (d, 2H, J=5 Hz).

Example 13

1-[5-Methyl-1-(2-pyrimidinyl)-4-pyrazolyl]-3-[4-(3-trifluoromethylphenyl)-1-piperazinyl]-1-trans-propene hydrochloride The procedures of Example 6 (1) and (2) were repeated but substituting the 1,2,3,4-tetrahydroisoquinoline hydrochloride employed in Example 6 (1) by 730 mg of 1-(3-trifluoromethylphenyl)piperazine hydrochloride. After the completion of the post treatment, 75 mg of the title compound was obtained.

mp.: 196°–201° C. (decomp.); NMR (in DSMO-$d_6$) δ: 2.65 (s, 3H), 3.1–3.3 (m, 4H), 3.5–3.7 (m, 2H), 3.9–4.1 (m, 4H), 6.24 (dt, 1H, J=16, 8 Hz) 6.83 (d, 1H, J=16 Hz) 7.15 (d, 1H, J=8 Hz), 7.26 (s, 1H), 7.28 (d, 1H, J=8 Hz), 7.47 (t, 1H, J=8 Hz), 7.52 (t, 1H, J=5 Hz), 8.07 (s, 1H), 8.91 (d, 2H, J=5 Hz).

Example 14

1-[5-Methyl-1-(2-pyrimidinyl)-4-pyrazolyl]-3-[4-(3-bromophenyl)-1-piperazinyl]-1-trans-propene hydrochloride The procedures of Example 6 (1) and (2) were repeated but substituting the 1,2,3,4-tetrahydroisoquinoline hydrochloride employed in Example 6 (1) by 580 mg of 1-(3-methylphenyl)piperazine hydrochloride. After the completion of the post treatment, 88 mg of the title compound was obtained.

m.p.: 200°–202° C. (decomp.); NMR (in DSMO-$d_6$) δ: 2.27 (s, 3H), 2.63 (s, 3H), 3.0–3.3 (m, 4H), 3.5–3.7 (m, 2H), 3.7–3.9 (m, 2H), 3.9–4.0 (m, 2H), 6.23 (dt, 1H, J=16, 7 Hz), 6.69 (d, 1H, J=8 Hz), 6.80 (d; 1H, J=16 Hz), 6.82 (s, 1H), 6.83 (d, 1H, J=8 Hz), 7.14 (t, 1H, J=8 Hz), 7.53 (t, 1H, J=5 Hz), 8.08 (s, 1H), 8.92 (d, 2H, J=5 Hz).

Example 15

1-[5-Methyl-1-(2-pyrimidinyl)-4-pyrazolyl]-3-[4-(3-bromophenyl)-1-piperazinyl]-1-trans-propene hydrochloride (1) 1-(3-Bromophenyl piperazine 100 ml of a solution of 10 g of 3-bromoaniline and 10.4 g of bis(2-chloroethyl)amine hydrochloride in 1-butanol was heated under reflux for 48 hours. After adding 6.16 g of sodium carbonate, the mixture was further heated under reflux for 72 hours. After cooling, the insoluble matters were collected by filtration, suspended in an aqueous solution of sodium hydroxide and extracted with chloroform. The extract was washed successively with water and a saturated aqueous solution of sodium chloride, and dried over anhydrous sodium sulfate. After evaporating the solvent, 10.05 g of the title compound was obtained in the form of an orange oily product. $^1$H-NMR (CDCl$_3$) δ: 2.9–3.1 (m, 4H), 3.1–3.3 (m, 4H), 6.83 (dd, 1H, J=8, 2 Hz), 6.95 (ddd, 1H, J=8, 2, 1 Hz), 7.03 (t, 1H, J=2 Hz), 7.10 (t, 1H, J=8 Hz).

(2) 1-[5-Methyl-1-(2-pyrimidinyl)-4-pyrazolyl]-3-[4-(3-bromophenyl)-1-piperazinyl]-1-propanone 2.42 g of 4-acetyl-1-(2-pyrimidinyl)-5-methylpyrazole, 2.89 g of the compound obtained in the above (1) and 12 ml of a 1N hydrochloric acid/ethanol solution were dissolved in 150 ml of ethanol and heated under reflux for 32 hours. During this period, 10 g of paraformaldehyde was added thereto in portions. The reaction mixture was evaporated and the residue was neutralized by adding an aqueous solution of sodium hydroxide. After extracting with chloroform, the extract was washed with a saturated aqueous solution of sodium chloride and dried over anhydrous sodium sulfate. After evaporating the solvent, the residue was purified by silica gel column chromatography (chloroform:methanol= 100:1) to thereby give 2.17 g of the title compound in the form of a solid product. $^1$H-NMR (CDCl$_3$) δ: 2.67 (t, 4H, J=5 Hz), 2.88 (t, 2H, J=7 Hz), 3.00 (s, 3H), 3.09 (t, 2H, J=7 Hz), 3.21 (t, 4H, J=5 Hz), 6.83 (dd, 1H, J=8, 2 Hz), 6.95 (ddd, 1H, J=8, 2, 1 Hz), 7.03 (t, 1H, J=2 Hz), 7.10 (t, 1H, J=8 Hz), 7.35 (t, 1H, J=5 Hz), 8.15 (s, 1H), 8.86 (d, 2H, J=5 Hz).

(3) 1-[5-Methyl-1-(2-pyrimidinyl)-4-pyrazolyl]-3-[4-(3-bromophenyl)-1-piperazinyl]-1-trans-propene hydrochloride 2 g of the compound obtained in the above (2) was dissolved in a solvent mixture comprising 50 ml of ethanol and 50 ml of tetrahydrofuran. Under ice-cooling, 1.2 g of sodium boron hydride was added thereto in portions for 8 hours. Then the reaction mixture was quenched with conc. hydrochloric acid. After evaporating the solvent, the residue was dissolved in 150 ml of tetrahydrofuran and 1.7 g of tosic acid monohydrate was added thereto followed by heating under reflux for 60 minutes. After evaporating the solvent, the residue was neutralized by adding an aqueous solution of sodium hydroxide and then extracted with ethyl acetate. The extract was washed with a saturated aqueous solution of sodium chloride and dried over anhydrous sodium sulfate. After evaporating the solvent, the residue was purified by silica gel column chromatography (chloroform:methanol= 100:1). Then the product was converted into hydrochloride with the use of 2.8 ml of a 1N hydrochloric acid/ethanol solution and recrystallized from ethanol to thereby give 876 mg of the title compound in the form of a colorless solid product. $^1$H-NMR (CDCl$_3$) δ: 2.62 (s, 3H), 3.0–3.2 (m, 4H), 3.5–3.6 (m, 2H), 3.8–4.0 (m, 4H), 6.23 (dt, 1H, J=16, 8 Hz), 6.82 (d, 1H, J=16 Hz), 7.01 (dd, 2H, J=8, 2 Hz), 7.19 (d, 1H, J=8 Hz), 7.20 (t, 1H, J=8 Hz), 7.53 (t, 1H, J=5 Hz), 8.08 (s, 1H), 8.92 (d, 2H, J=5 Hz).

Example 16

1-[5-Methyl-1-(4,6-dimethyl-2-pyrimidinyl)-4-pyrazolyl]-3-[4-(3,4-dichlorophenyl)-1-piperazinyl]-1-trans-propene hydrochloride 1.0 g of 1-[5-methyl-1-(4,6-dimethyl-2-pyrimidinyl)-4-pyrazolyl]-3-[4-(3,4-dichlorophenyl)-1-piperazinyl]-1-propanone hydrochloride was dissolved in a solvent mixture comprising 50 ml of ethanol and 50 ml of tetrahydrofuran. After cooling with ice to 0° C., 500 mg of sodium boron hydride was added and the mixture was stirred at the same temperature for 45 minutes. Further, 50 mg of sodium boron hydride was added and the mixture was stirred for additional 2 hours. Then it was neutralized by adding a 1N hydrochloric acid/ethanol solution. After evaporating the ethanol, chloroform was added to the concentrated residue. Then it was washed with a saturated aqueous solution of sodium hydrogencarbonate and a saturated aqueous solution of sodium chloride, and dried over anhydrous sodium sulfate. After evaporating the solvent, 50 ml of dioxane, 50 ml of tetrahydrofuran and 220 mg of p-toluenesulfonic acid monohydrate were added to the obtained residue. Then the resulting mixture was heated under reflux for 5 hours. After evaporating the solvent, chloroform was added to the residue. Then it was washed with a saturated aqueous solution of sodium hydrogencarbonate and a saturated aqueous solution of sodium chloride, and dried over anhydrous sodium sulfate. After evaporating the solvent, the residue was purified by silica gel column chromatography (chloroform:methanol=30:1), converted into hydrochloride by adding a 1N hydrochloric acid/ethanol solution and recrystallized from ethanol to thereby give 560 mg of the title compound.

m.p.: 206°–210° C. (decomp.); $^1$H-NMR (DMSO-$d_6$) δ: 2.51 (s, 6H), 2.60 (s, 3H), 3.1–3.25 (m, 4H), 3.5–3.6 (m, 2H), 3.9–4.05 (m, 4H), 6.22 (dt, 1H, J=15.6, 7.3 Hz), 6.80 (d, 1H, J=15.6 Hz), 7.01 (dd, 1H, J=8.8, 3.0 Hz), 7.25 (s, 1H), 7.29 (s, 1H), 7.46 (d, 1H, J=8.8 Hz), 8.03 (s, 1H).

Example 17

1-[5-Methyl-1-(4,6-dimethyl-2-pyrimidinyl)-4-pyrazolyl]-3-[4-(3,5-dichlorophenyl)-1-piperazinyl]-1-trans-propene hydrochloride By using 1.0 g of 1-[5-methyl-1-(4,6-dimethyl-2-pyrimidinyl)-4-pyrazolyl]-3-[4-(3,5-dichlorophenyl)-1-piperazinyl]-1-propanone hydrochloride, the procedure of Example 16 was repeated. After the completion of the post treatment, 654 mg of the title compound was obtained.

m.p.: 212°–218° C. (decomp.); $^1$H-NMR (DMSO-$d_6$) δ: 2.51 (s, 6H), 2.60 (s, 3H), 3.05–3.3 (m, 4H), 3.45–3.55 (m, 2H), 3.9–4.05 (m, 4H), 6.21 (dt, 1H, J=15.6, 7.3 Hz), 6.80 (d, 1H, J=15.6 Hz), 6.96 (s, 1H), 7.06 (s, 2H), 7.29 (s, 1H), 8.03 (s, 1H).

Example 18

1-[5-Methyl-1-(4-hydroxy-6-methyl-2-pyrimidinyl)-4-pyrazolyl]-3-[4-(2-methylphenyl)-1-piperazinyl]-1-trans-propene hydrochloride (1) 1-[5-Methyl-1-(4-hydroxy-6-methyl-2-pyrimidinyl)-4-pyrazolyl]-3-[4-(2-methylphenyl)-1-piperazinyl]-1-propanone hydrochloride 300 mg of boron tribromide was added to 3 ml of methylene chloride and the obtained solution was cooled. Into the solution was dropped a solution of 470 mg of 1-[5-methyl-1-(4-methoxy-6-methyl-2-pyrimidinyl)-4-pyrazolyl]-3-[4-(2-methylphenyl)-1-piperazinyl]-1-propanone hydrochloride in 100 ml of methylene chloride. After stirring at room temperature for 72 hours, water was added and the mixture was extracted with methylene chloride twice. The organic layer was washed with a saturated aqueous solution of sodium hydrogencarbonate and a saturated aqueous solution of sodium chloride, and dried over anhydrous sodium sulfate. After evaporating the solvent, the residue was purified by silica gel column chromatography (silica gel 800 g, chloroform:methanol=10:1–5:1). Then the obtained product was converted into hydrochloride by adding a 1N hydrochloric acid/ethanol solution and recrystallized from ethanol to thereby give 150 mg of the title compound.

m.p.: 208°–211° C. (decomp.); $^1$H-NMR (DMSO-$d_6$) δ: 2.28 (s, 3H), 2.38 (s, 3H), 2.83 (s, 3H), 3.05–3.35 (m, 6H), 3.45–3.65 (m, 6H), 6.56 (brs, 1H), 7.04 (m, 2H), 7.19 (m, 2H), 8.39 (s, 1H).

(2) 1-[5-Methyl-1-(4-hydroxy-6-methyl-2-pyrimidinyl)-4-pyrazolyl]-3-[4-(2-methylphenyl)-1-piperazinyl]-1-trans-propene hydrochloride By using 130 mg of the compound obtained in the above (1), the procedure of Example 16 was repeated. After the completion of the post treatment, 27 mg of the title compound was obtained.

m.p.: 220°–225° C. (decomp.); $^1$H-NMR (DMSO-$d_6$) δ: 2.27 (s, 3H), 2.31 (s, 3H), 2.64 (s, 3H), 3.0–3.15 (m, 2H), 3.15–3.3 (m, 4H), 3.5–3.6 (m, 2H), 3.95–4.05 (m, 2H), 6.25 (dt, 1H, J=15.6, 6.8 Hz), 6.33 (brs, 1H), 6.83 (d, 1H, J=15.6 Hz), 7.03 (m, 2H), 7.19 (m, 2H), 8.12 (s, 1H).

Example 19

1-[5-Methyl-1-(2-pyrimidinyl)-4-pyrazolyl]-3-[4-(2-pyridyl)-1-piperazinyl]-1-trans-propene hydrochloride (1) 1-[5-Methyl-1-(2-pyrimidinyl)-4-pyrazolyl]-3-[4-(2-pyridyl)-1-piperazinyl]-1-propanone hydrochloride 606 mg of 4-acetyl-1-(2-pyrimidinyl)-5-methylpyrazole was dissolved in 60 ml of ethanol and 490 mg of 2-pyridylpiperazine hydrochloride and 270 mg of paraformaldehyde were added thereto. The obtained mixture was heated under reflux for 24 hours. Further, 100 mg of paraformaldehyde was added and the obtained mixture was heated under reflux for 60 hours. Then the ethanol was almost halved by evaporation and the precipitate was filtered. To the precipitate was added chloroform. Next, it was washed with a saturated aqueous solution of sodium hydrogencarbonate and a saturated aqueous solution of sodium chloride, and dried over anhydrous sodium sulfate followed by evaporation. The residue was purified by silica gel column chromatography (silica gel 50 g, chloroform:methanol=50:1–40:1). Then the obtained product was converted into hydrochloride by adding 1N hydrochloric acid and recrystallized from ethanol to thereby give 300 mg of the title compound.

m.p.: 218°–224° C. (decomp.); $^1$H-NMR (DMSO-$d_6$) δ: 2.83 (s, 3H), 3.1–3.25 (m, 2H), 3.3–3.8 (m, 8H), 4.4–4.5 (m, 2H), 6.86 (t, 1H, J=5 Hz), 7.15 (d, 1H, J=8.8 Hz), 7.66 (t, 1H, J=4.9 Hz), 7.78 (m, 1H), 8.16 (d, 1H, J=5 Hz), 8.41 (s, 1H), 9.00 (d, 2H, J=4.9 Hz).

(2) 1-[5-Methyl-1-(2-pyrimidinyl)-4-pyrazolyl]-3-[4-(2-pyridyl)-1-piperazinyl]-1-trans-propene hydrochloride By using 260 mg of the compound obtained in the above (1), the procedure of Example 16 was repeated. After the completion of the post treatment, 51 mg of the title compound was obtained.

m.p.: 218°–224° C. (decomp.); $^1$H-NMR (DMSO-$d_6$) δ: 2.62 (s, 3H), 3.05–3.15 (m, 2H), 3.25–3.35 (m, 2H), 3.5–3.6 (m, 2H), 3.9–4.0 (m, 2H), 4.35–4.45 (m, 2H), 6.21 (dt, 1H, J=16, 6.81 (t, 1H, J=5 Hz), 6.82 (d, 1H, J=16 Hz), 7.07 (d, 1H, J=8.8 Hz), 7.53 (t, 1H, J=4.9 Hz), 8.08 (s, 1H), 8.16 (d, 1H, J=5 Hz), 8.91 (d, 2H, J=4.9 Hz).

Example 20

1-[5-Methyl-1-(4-methoxy-2-pyrimidinyl)-4-pyrazolyl]-3-[4-(3-chlorophenyl)-1-piperazinyl]-1-trans-propene hydrochloride (1) 1-[5-Methyl-1-(4-methoxy-2-pyrimidinyl)-4-pyrazolyl]-3-[4-(3-chlorophenyl)-1-piperaziny]-1-propanone hydrochloride By using 2.32 g of 4-acetyl-1-(4-methoxy-2-pyrimidinyl)-5-methylpyrazole and 2.33 g of 3-chlorophenylpiperazine hydrochloride, the procedure of Example 19 (1) was repeated. After the completion of the post treatment, 1.50 g of the title compound was obtained.

m.p.: 194°–197° C. (decomp.); $^1$H-NMR (DMSO-$d_6$) δ: 2.84 (s, 3H), 3.05–3.25 (m, 4H), 3.45–3.55 (m, 2H), 3.55–3.65 (m, 2H), 3.85–3.95 (m, 2H), 4.00 (s, 3H), 6.88 (d, 1H, J=8 Hz), 6.99 (d, 1H, J=8 Hz), 7.07 (d, 1H, J=6 Hz), 7.09 (s, 1H), 7.27 (t, 1H, J=8 Hz), 8.41 (s, 1H), 8.67 (d, 1H, J=6 Hz).

(2) 1-[5-Methyl-1-(4-methoxy-2-pyrimidinyl)-4-pyrazolyl]-3-[4-(3-chlorophenyl)-1-piperazinyl]-1-trans-propene hydrochloride By using 0.47 g of the compound obtained in the above (1), the procedure of Example 16 was repeated. After the completion of the post treatment, 256 mg of the title compound was obtained.

m.p.: 181°–184° C. (decomp.); $^1$H-NMR (DMSO-d$_6$) δ: 2.67 (s, 3H), 3.1–3.25 (m, 4H), 3.5–3.6 (m, 2H), 3.85–3.95 (m, 4H), 4.00 (s, 3H), 6.23 (dt, 1H, J=16, 7 Hz), 6.83 (dt, 1H, J=16 Hz), 6.87 (d, 1H, J=8 Hz), 6.92 (d, 1H, J=5 Hz), 6.97 (dd, 1H, J=8, 2 Hz), 7.05 (s, 1H), 7.26 (t, 1H, J=8 Hz), 8.07 (d, 1H, J=5 Hz), 8.58 (s, 1H).

Example 21

1-[5-Methyl-1-(4-hydroxy-2-pyrimidinyl)-4-pyrazolyl]-3-[4-(3-chlorophenyl)-1-piperazinyl]-1-trans-propene hydrochloride (1) 1-[5-Methyl-1-(4-hydroxy-2-pyrimidinyl)-4-pyrazolyl]-3-[4-(3-chlorophenyl)-1-piperazinyl]-1-propanone hydrochloride By using 950 mg of 1-[5-methyl-1-(4-methoxy-2-pyrimidinyl)-4-pyrazolyl]-3-[4-(3-chlorophenyl)-1-piperazinyl]-1-propanone hydrochloride, the procedure of Example 19 (1) was repeated. After the completion of the post treatment, 167 mg of the title compound was obtained.

m.p.: 177°–181° C. (decomp.); $^1$H-NMR (DMSO-d$_6$) δ: 2.84 (s, 3H), 3.85–3.95 (m, 2H), 3.9–4.0 (m, 2H), 6.88 (d, 1H, J=7.8 Hz), 6.64 (d, 1H, J=6 Hz), 6.87 (d, 1H, J=8 Hz), 6.98 (d, 1H, J=8 Hz), 7.08 (s, 1H), 7.26 (t, 1H, J=8 Hz), 8.31 (d, 1H, J=6 Hz), 8.42 (s, 1H).

(2) 1-[5-Methyl-1-(4-hydroxy-2-pyrimidinyl)-4-pyrazolyl]-3-[4-(3-chlorophenyl)-1-piperazinyl]-1-trans-propene hydrochloride By using 147 mg of the compound obtained in the above (1), the procedure of Example 16 was repeated. After the completion of the post treatment, 86 mg of the title compound was obtained.

m.p.: 197°–201° C. (decomp.); $^1$H-NMR (DMSO-d$_6$) δ: 2.64 (s, 3H), 3.05–3.25 (m, 4H), 3.5–3.6 (m, 2H), 3.85–4.0 (m, 4H), 6.26 (dt, 1H, J=16, 7 Hz), 6.39 (d, 1H, J=5 Hz), 6.82 (d, 1H, J=16 Hz), 6.87 (d, 1H, J=8 Hz), 6.97 (d, 1H, J=8 Hz), 7.05 (s, 1H), 7.26 (t, 1H, J=8 Hz), 8.09 (d, 1H, J=5 Hz), 8.15 (s, 1H).

Example 22

1-[5-Methyl-1-(4,6-dimethyl-2-pyrimidinyl)-4-pyrazolyl]-3-[4-(2,3-dichlorophenyl)-1-piperazinyl]-1-trans-propene hydrochloride By using 710 mg of 1-[5-methyl-1-(4,6-dimethyl-2-pyrimidinyl)-4-pyrazolyl]-3-[4-(2,3-dichlorophenyl)-1-piperazinyl]-1-propanone hydrochloride, the procedure of Example 16 was repeated. After the completion of the post treatment, 515 mg of the title compound was obtained.

m.p.: 205°–208° C. (decomp.); $^1$H-NMR (DMSO-d$_6$) δ: 2.51 (s, 6H), 2.62 (s, 3H), 3.1–3.3 (m, 4H), 3.4–3.5 (m, 2H), 3.5–3.65 (m, 2H), 3.95–4.05 (m, 2H), 6.22 (dt, 1H, J=16.1, 7.3 Hz), 6.83 (d, 1H, J=16.1 Hz), 7.18 (d, 1H, J=8 Hz), 7.28 (s, 1H), 7.35 (t, 1H, J=8 Hz), 7.37 (d, 1H, J=8 Hz), 8.03 (s, 1H).

Example 23

1-[5-Methyl-1-(4 6-dimethyl-2-pyrimidinyl)-4-pyrazolyl]-3-[4-(2-chlorophenyl)-1-piperazinyl]-1-trans-propene hydrochloride By using 1.48 g of 1-[5-methyl-1-(4,6-dimethyl-2-pyrimidinyl)-4-pyrazolyl]-3-[4-(2-chlorophenyl)-1-piperazinyl]-1-propanone hydrochloride, the procedure of Example 16 was repeated. After the completion of the post treatment, 1.29 g of the title compound was obtained.

m.p.: 201°–206° C. (decomp.); $^1$H-NMR (DMSO-d$_6$) δ: 2.51 (s, 6H), 2.61 (s, 3H), 3.1–3.25 (m, 4H), 3.4–3.5 (m, 2H), 3.55–3.65 (m, 2H), 3.95–4.05 (m, 21H), 6.22 (dt, 1H, J=15.6, 7.3 Hz), 6.83 (d, 1H, J=15.6 Hz), 7.12 (t, 1H, J=7 Hz), 7.22 (d, 1H, J=7 Hz), 7.29 (s, 1H), 7.35 (t, 1H, J=7 Hz), 7.46 (d, 1H, J=7 Hz), 8.04 (s, 1H).

Example 24

1-[5-Methyl-1-(2-pyrimidinyl)-4-pyrazolyl]-3-[4-(2-pyrimidinyl)-1-piperazinyl]-1-trans-propene dihydrochloride (1) 1-[5-Methyl-1-(2-pyrimidinyl)-4-pyrazolyl]-3-[4-(2-pyrimidinyl)-1-piperazinyl]-1-propanone dihydrochloride 404 mg of 4-acetyl-1-(2-pyrimidinyl)-5-methylpyrazole and 474 mg of 1-(2-pyrimidinyl)piperazine dihydrochloride were dissolved in 15 ml of ethanol and heated under reflux for 23 hours. During this period, 900 mg of paraformaldehyde was added thereto in portions. The reaction mixture was cooled, and the precipitate thus formed was taken up by filtration and washed with methanol. Thus 327 mg of the title compound was obtained in the form of a colorless solid product.

$^1$H-NMR (DMSO-d$_6$) δ: 2.81 (s, 3H), 3.0–3.2 (m, 2H), 3.3–3.4 (m, 2H), 3.4–3.5 (m, 2H), 3.5–3.6 (m, 2H), 3.6–3.7 (m, 2H), 4.6–4.8 (m, 2H), 6.78 (t, 1H, J=5 Hz), 7.66 (t, 1H, J=5 Hz), 8.40 (s, 1H), 8.46 (d, 2H, J=5 Hz), 9.00 (d, 2H, J=5 Hz).

(2) 1-[5-Methyl-1-(2-pyrimidinyl)-4-pyrazolyl]-3-[4-(2-pyrimidinyl)-1-piperazinyl]-1-trans-propene dihydrochloride 200 mg of the compound obtained in the above (1) was dissolved in a solvent mixture comprising 8 ml of ethanol and 8 ml of tetrahydrofuran. Under-ice-cooling, 160 mg of sodium boron hydride was added thereto in portions for 130 minutes. Then the reaction mixture was quenched with conc. hydrochloric acid. After evaporating the solvent, the residue was dissolved in 10 ml of tetrahydrofuran and 201 mg of tosic acid monohydrate was added thereto followed by heating under reflux for 30 minutes. After evaporating the solvent, an aqueous solution of sodium hydroxide was added to the residue followed by extraction with ethyl acetate. The extract was washed with a saturated aqueous solution of sodium chloride and dried over anhydrous sodium sulfate. After evaporating the solvent, the residue was purified by silica gel column chromatography (chloroform:methanol= 100:2). Then the product was converted into hydrochloride with the use of a 1N hydrochloric acid/ethanol solution and recrystallized from methanol/ethyl acetate to thereby give 29 mg of the title compound as a colorless solid product.

m.p.: 130°–140° C.; $^1$H-NMR (DMSO-d$_6$) δ: 2.61 (s, 3H), 3.0–3.2 (m, 2H), 3.3–3.5 (m, 2H), 3.5–3.6 (m, 2H), 3.9–4.0 (m, 2H), 4.7–4.8 (m, 2H), 6.21 (dt, 1H, J=17, 8 Hz), 6.77 (t, 1H, J=5 Hz), 6.80 (d, 1H, J=17 Hz), 7.54 (t, 1H, J=5 Hz), 8.07 (s, 1H), 8.45 (d, 2H, J=5 Hz), 8.92 (d, 2H, J=5 Hz).

Example 25

1-[5-Methyl-1-(4,6-dimethyl-2-pyrimidinyl)-4-pyrazolyl]-3-[4-(2,5-dichlorophenyl)-1-piperazinyl]-1-trans-propene hydrochloride By using 1.53 g of 1-[5-methyl-1-(4,6-dimethyl-2-pyrimidinyl)-4-pyrazolyl]-3-[4-(2,5-dichlorophenyl)-1-piperazinyl]-1-propanone hydrochloride, the procedure of Example 16 was repeated. After the completion of the post treatment, 840 mg of the title compound was obtained.

m.p.: 198°–201° C. (decomp.); $^1$H-NMR (DMSO-d$_6$) δ: 2.51 (s, 6H), 2.61 (s, 3H), 3.1–3.25 (m, 4H), 3.45–3.65 (m, 4H), 3.95–4.05 (m, 2H), 6.22 (dt, 1H, J=15.6; 7.3 Hz), 6.83 (d, 1H, J=15.6 Hz), 7.18 (dd, 1H, J=8.3, 2.0 Hz), 7.26 (s, 1H), 7.29 (s, 1H), 7.49 (d, 1H, J=8.3 Hz), 8.04 (s, 1H).

Example 26

1-[5-Methyl-1-(4,6-dimethyl-2-pyrimidinyl)-4-pyrazolyl]-3-[4-(2,4-dichlorophenyl)-1-piperazinyl]-1-trans-propene hydrochloride By using 408 mg of 1-[5-methyl-1-(4,6-dimethyl-2-pyrimidinyl)-4-pyrazolyl]-3-[4-(2,4-dichlorophenyl)-1- piperazinyl]-1-propanone hydrochloride, the procedure of Example 16 was repeated. After the completion of the post treatment, 131 mg of the title compound was obtained.

m.p.: 212°–216° C. (decomp.); $^1$H-NMR (DMSO-d$_6$) δ: 2.51 (s, 6H), 2.61 (s, 3H), 3.1–3.25 (m, 4H), 3.4–3.5 (m, 2H), 3.55–3.65 (m, 2H), 3.9–4.0 (m, 2H), 6.22 (dt, 1H, J=15.6, 7.3 Hz), 6.82 (d, 1H, J=15.6 Hz), 7.24 (d, 1H, J=8.8 Hz), 7.29 (s, 1H), 7.41 (dd, 1H, J 8.8, 1.5 Hz), 7.61 (s, 1H), 8.03 (s, 1H).

Example 27

1-[5-Methyl-1-(2-pyrimidinyl)-4-pyrazolyl]-3-[4-(3,5-dichlorophenyl)-1-pyrazinyl]-1-trans-propene hydrochloride (1) 1-[5-Methyl-1-(2-pyrimidinyl)-4-pyrazolyl]-3-[4-(3,5-dichlorophenyl)-1-piperazinyl]-1-propanone hydrochloride 1.75 g of 4-acetyl-1-(2-pyrimidinyl)-5-methylpyrazole was dissolved in 150 ml of ethanol and 2.21 g of 3,5-dichlorophenylpiperazine hydrochloride and 740 mg of paraformaldehyde were added thereto. The obtained mixture was heated under reflux for 24 hours. Further, 300 mg of paraformaldehyde was added and the obtained mixture was heated under reflux for 15 hours. Then the ethanol was almost halved by evaporation and the precipitate was filtered followed by the addition of chloroform thereto. Next, it was washed with a saturated aqueous solution of sodium hydrogencarbonate and a saturated aqueous solution of sodium chloride, and dried over anhydrous sodium sulfate. After evaporating the solvent, the residue was purified by silica gel column chromatography (silica gel 90 g, chloroform:methanol=50:1). Then the obtained product was converted into hydrochloride by adding 1N hydrochloric acid and recrystallized from ethanol to thereby give 1.82 g of the title compound.

m.p.: 208°–211° C. (decomp.); $^1$H-NMR (DMSO-d$_6$) δ: 2.82 (s, 3H), 3.1–3.25 (m, 4H), 3.45–3.6 (m, 4H), 3.6–3.7 (m, 2H), 3.95–4.05 (m, 2H); 6.96 (s, 1H), 7.08 (s, 2H), 7.67 (t, 1H, J=4.9 Hz), 8.42 (s, 1H), 9.00 (d, 2H, J=4.9 Hz).

(2) 1-[5-Methyl-1-(2-pyrimidinyl)-4-pyrazolyl]-3-[4-(3,5-dichlorophenyl)-1-piperazinyl]-1-trans-propene hydrochloride By using 1.45 g of 1-[5-methyl-1-(2-pyrimidinyl)-4-pyrazolyl]-3-[4-(3,5-dichlorophenyl)-1-piperazinyl]-1-propanone hydrochloride, the procedure of Example 16 was repeated. After the completion of the post treatment, 358 mg of the title compound was obtained.

m.p.: 209°–212° C. (decomp.); $^1$H-NMR (DMSO-d$_6$) δ: 2.62 (s, 3H), 3.05–3.25 (m, 4H), 3.5–3.6 (m, 2H), 3.9–4.05 (m, 4H), 6.21 (dt, 1H, J=15.6, 7.8 Hz), 6.81 (d, 1H, J=15.6 Hz), 6.95 (s, 1H), 7.05 (s, 2H), 7.53 (t, 1H, J=4.9 Hz), 8.08 (s, 1H), 8.92 (d, 2H, J=4.9 Hz).

Example 28

1-[5-Methyl-1-(2-pyrimidinyl)-4-pyrazolyl]-3-[4-(3,5-difluorophenyl)-1-piperazinyl]-1-trans-propene hydrochloride (1) 3,5-Difluorophenylpiperazine hydrochloride 13.7 g of bis-(2-chloroethyl)amine was suspended in 120 ml of butanol. To the obtained solution was added 10 g of 3,5-difluoroaniline and the mixture was heated under reflux for 48 hours. After cooling, 10.6 g of potassium carbonate was added and the obtained mixture was heated under reflux for additional 24 hours. Then crystals were collected by filtration, dissolved in water, extracted with chloroform, successively washed with water and a saturated aqueous solution of sodium chloride, and dried over anhydrous sodium sulfate. After evaporating the solvent, the residue was dissolved in a small amount of chloroform and converted into hydrochloride by adding a 4N hydrochloric acid/dioxane solution. After filtration, 12.6 g of the title compound was obtained.

m.p.: 234°–238° C. (decomp.); $^1$H-NMR (DMSO-d$_6$) δ: 3.1–3.2 (m, 4H), 3.4–3.5 (m, 4H), 6.56 (t, 2H, J=9.3 Hz), 6.70 (d, 1H, J=9.3 Hz).

(2) 1-[5-Methyl-1-(2-pyrimidinyl)-4-pyrazolyl]-3-[4-(3,5-difluorophenyl)-1-piperazinyl]-1-propanone hydrochloride 1.01 g of 4-acetyl-1-(2-pyrimidinyl)-5-methylpyrazole was dissolved in 85 ml of anhydrous ethanol and 1.10 g of the compound obtained in the above (1) and 0.45 g of paraformaldehyde were added thereto. After heating under reflux for 24 hours, 0.20 g of paraformaldehyde was further added thereto and the obtained mixture was heated under reflux for additional 60 hours. Then the ethanol was evaporated and chloroform was added to the residue. Next, it was washed with a saturated aqueous solution of sodium chloride and dried over anhydrous sodium sulfate. After evaporating the solvent, the residue was purified by silica gel column chromatography (silica gel 50 g, chloroform:methanol= 50:1–40:1). Then the product was converted into hydrochloride by adding a 1N hydrochloric acid/ethanol solution and recrystallized from ethanol. Thus 129 mg of the title compound was obtained.

m.p.: 195°–200° C. (decomp.); $^1$H-NMR (DMSO-d$_6$) δ: 2.82 (s, 3H), 3.1–3.25 (m, 4H), 3.45–3.55 (m, 4H), 3.6–3.7 (m, 2H), 3.95–4.05 (m, 2H), 6.58 (t, 1H, J=8.8 Hz), 6.77 (d, 2H, J=10.3 Hz), 7.67 (t, 1H, J=4.9 Hz), 8.42 (s, 1H), 9.01 (d, 2H, J=4.9 Hz).

(3) 1-[5-Methyl-1-(2-pyrimidinyl)-4-pyrazolyl]-3-[4-(3,5-difluorophenyl)-1-piperazinyl]-1-trans-propene hydrochloride By using 103 mg of the compound obtained in the above (2), the procedure of Example 16 was repeated. After the completion of the post treatment, 39 mg of the title compound was obtained.

m.p.: 189°–193° C. (decomp.); $^1$H-NMR (DMSO-d$_6$) δ: 2.62 (s, 3H), 3.05–3.25 (m, 4H), 3.5–3.6 (m, 2H), 3.9–4.05 (m, 4H), 6.21 (dt, 1H, J=15.1, 7.3 Hz), 6.58 (t, 1H, J=9.3 Hz), 6.76 (d, 2H, J=9.3 Hz), 6.81 (d, 1H, J=15.6 Hz), 7.54 (t, 1H, J=4.9 Hz), 8.10 (s, 1H), 8.92 (d, 2H, J=4.9 Hz).

Example 29

1-[5-Methyl-1-(2-pyrimidinyl)-4-pyrazolyl]-3-[4-phenyl-1,2,3,6-tetrahydro-1-pyridyl]-1-propene 207 mg of 1-[5-methyl-1-(2-pyrimidinyl)-4-pyrazolyl]-3-[4-phenyl-1,2,3,6-tetrahydro-1-pyridyl]-1-propanone hydrochloride was dissolved in a solvent mixture comprising 10 ml of ethanol and 10 ml of tetrahydrofuran. After ice-cooling to 0° C., 319 mg of sodium boron hydride was added thereto in portions for 7 hours. After decomposing the sodium boron hydride by adding conc. hydrochloric acid, the solvent was removed by evaporation. Then the residue was neutralized by adding an aqueous solution of sodium hydroxide and extracted with chloroform. The extract was washed with a saturated aqueous solution of sodium chloride and dried over anhydrous sodium sulfate. After evaporating the solvent, the residue was dissolved in 7 ml of tetrahydrofuran. Then 250 mg of tosic acid monohydrate was added and the mixture was heated under reflux for 60 minutes. After evaporating the solvent, the residue was neutralized by adding an aqueous solution of sodium hydroxide and extracted with ethyl acetate. The extract was washed with a saturated aqueous solution of sodium chloride and dried over anhydrous sodium sulfate. After evaporating the solvent, the residue was purified by silica gel column chromatography (chloroform:methanol=100:1–3). Then the product was converted into hydrochloride by adding 0.3 ml of a 1N hydrochloric acid/ethanol solution and recrystallized from methanol/ethyl acetate. Thus 47 mg of the title compound was obtained in the form of a pale yellow solid product.

m.p.: 112°–114° C.; $^1$H-NMR (DMSO-d$_6$) δ: 2.63 (s, 3H), 2.7–2.9 (m, 1H), 2.8–3.0 (m, 1H), 3.2–3.2 (m, 1H), 3.6–3.7 (m, 1H), 3.7–3.9 (m, 1H), 3.9–4.1 (m, 2H), 6.22 (bs, 1H), 6.26 (dt, 1H, J=16, 8 Hz), 6.86 (d, 1H, J=16 Hz), 7.33 (t, 1H, J=7 Hz), 7.40 (t, 2H, J=7 Hz), 7.50 (d, 2H, J=7 Hz), 7.53 (t, 1H, J=5 Hz), 8.07 (s, 1H), 8.92 (d, 2H, J=5 Hz).

Example 30

1-[5-Methyl-1-(2-pyrimidinyl)-4-pyrazolyl]-3-[4-(3-nitrophenyl)-1-piperazinyl]-1-trans-propene hydrochloride (1) 1-(3-Nitrophenyl)piperazine 50 ml of a solution of 5 g of 3-nitroaniline and 6.46 g of bis(2-chloroethyl)amine hydrochloride in 1-butanol was heated under reflux for 25 hours. After adding 3.84 g of sodium carbonate, the mixture was further heated under reflux for 60 hours. After allowing to cool, the insoluble matters were collected by filtration, suspended in an aqueous solution of sodium hydroxide and extracted with chloroform. The extract was successively washed with water and a saturated aqueous solution of sodium chloride, and dried over anhydrous sodium sulfate. After evaporating the solvent, the residue was purified by silica gel column chromatography (chloroform:methanol=100:3). Thus 4.03 g of the title compound was obtained in the form of a red oily product.

$^1$H-NMR (CDCl$_3$): 3.05 (t, 2H, J=5 Hz), 3.24 (t, 2H, J=5 Hz), 7.19 (dd, 1H, J=2, 8 Hz); 7.37 (t, 1H, J=8 Hz), 7.65 (dd, 1H, J=2, 8 Hz), 7.72 (t, 1H, J=2 Hz).

(2) 1-[5-Methyl-1-(2-pyrimidinyl)-4-pyrazolyl]-3-[4-(3-nitrophenyl)-1-piperazinyl]-1-propanone hydrochloride 487 mg of 4-acetyl-1-(2-pyrimidinyl)-5-methylpyrazole, 524 mg of the compound obtained in the above (1) and 3.6 ml of a 1N hydrochloric acid/ethanol solution were dissolved in 40 ml of ethanol and heated under reflux for 54 hours. During this period, 4.3 g of paraformaldehyde was added thereto in portions. After cooling, the insoluble matters were collected by filtration. Thus 630 mg of the title compound was obtained in the form of a yellow solid product.

$^1$H-NMR (DMSO-d6): 2.82 (s, 3H), 3.2–3.3 (m, 4H), 3.5–3.6 (m, 4H), 3.6–3.8 (m, 2H), 4.0–4.1 (m, 2H), 7.51 (dt, 1H, J=8, 2 Hz), 7.54 (t, 1H, J=8 Hz), 7.66 (t, 1H, J=5 Hz), 7.68 (dt, 1H, J=8, 2 Hz), 7.79 (t, 1H, J=2 Hz), 9.01 (d, 2H, J=5 Hz);

(3) 1-[5-Methyl-1-(2-pyrimidinyl)-4-pyrazolyl]-3-[4-(3-nitrophenyl)-1-piperazinyl]-1-trans-propene hydrochloride 200 mg of the compound obtained in the above (2) was dissolved in a solvent mixture comprising 10 ml of ethanol and 10 ml of tetrahydrofuran, and stirred for 2 hours under ice-cooling. During this period, 90 mg of sodium boron hydride was added thereto in portions. Then 1.4 ml of 20% hydrochloric acid was added. After distilling off the solvent, 20 ml of tetrahydrofuran and 210 mg of p-toluenesulfonic acid monohydrate were added to the residue. The mixture was heated under reflux for 20 minutes and the solvent was removed by evaporation. Then the residue was neutralized with an aqueous solution of sodium hydroxide and extracted with chloroform. The extract was successively washed with water and a saturated aqueous solution of sodium chloride and dried over anhydrous sodium sulfate. After evaporating the solvent, the residue was purified by silica gel column chromatography (chloroform:methanol=100:1). Then the product was converted into hydrochloride with a 1N hydrochloric acid/ethanol solution and recrystallized from etha-nol. Thus 64 mg of the title compound was obtained in the form of a yellow solid product.

m.p.: 189° C. (decomp.); $^1$H-NMR (DMSO-d$_6$): 2.63 (s, 3H), 3.1–3.3 (m, 4H), 3.2–3.4 (m, 4H), 3.9–4.1 (m, 4H), 6.23 (dt, 1H, J=16, 8 Hz), 6.82 (d, 1H, J=16 Hz), 7.48 (d, 1H, J=8 Hz), 7.54 (t, 1H, J=5 Hz), 7.54 (t, 1H, J=8 Hz), 7.67 (d, 1H, J=8 Hz), 7.76 (brs, 1H), 8. 09 (s, 1H), 8.92 (d, 2H1, J=5 Hz).

Example 31

1-[5-Methyl-1-(2-pyrimidinyl)-4-pyrazolyl]-3-[4-(3-acetylaminophenyl)-1-piperazinyl]-1-trans-propene hydrochloride (1) 1-[5-Methyl-1-(2-pyrimidinyl)-4-pyrazolyl]-3-[4-(3-acetylaminophenyl)-1-piperazinyl]-1-trans-propanone 404 mg of the compound obtained in Example 30 (2), 113 ml of acetic anhydride, 347 ml of triethylamine and 110 mg of 10% Pd/C were suspended in 22 ml of acetic acid and stirred in a hydrogen gas stream. Then the insoluble matters were eliminated by filtration. After evaporating the solvent, the residue was purified by silica gel column chromatography (chloroform:methanol=100:3). Thus 277 mg of the title compound was obtained.

$^1$H-NMR (CDCl$_3$): 2.16 (s, 3H), 2.6–2.7 (m, 4H), 2.89 (t, 2H, J=7 Hz), 3.00 (s, 3H), 3.10 (t, 2H, J=7 Hz), 3.1–3.3 (m, 4H), 6.6–7.3 (m, 4H), 7.35 (t, 1H, J=5 Hz), 8.14 (s, 1H), 8.86 (d, 2H, J=5 Hz).

(2) 1-[5-Methyl-1-(2-pyrimidinyl)-4-pyrazolyl]-3-[4-(3-acetylaminophenyl)-1-piperazinyl]-1-trans-propene hydrochloride By using 150 mg of the compound obtained in the above (1), the procedure of Example 30 (3) was repeated. After the completion of the post treatment, 16 mg of the title compound was obtained in the form of a yellow solid product.

m.p.: 200°–220° C. (decomp.); $^1$H-NMR (DMSO-d$_6$): 2.12 (s, 3H), 2.76 (s, 3H), 3.13 (t, 2H, J=12 Hz), 3.28 (t, 2H, J=12 Hz), 3.69 (d, 2H, J=12 Hz), 3.85 (dr 2H, J=12 Hz), 4.01 (d, 2H, J=7 Hz), 6.22 (dt, 1H, J=16, 8 Hz), 6.77 (dd, 1H, J=8, 2 Hz), 6.92 (d, 1H, J=16 Hz), 6.98 (d, 1H, J=8 Hz), 7.22 (t, 1H, J=8 Hz), 7.43 (t, 1H, J=5 Hz), 7.44 (d, 1H, J=2 Hz), 8.07 (s, 1H), 8.86 (d, 2H, J=5 Hz).

Example 32

1-[5-Methyl-1-(2-pyrimidinyl)-4-pyrazolyl]-3-[4-(3-cyanophenyl)-1-piperazinyl]-1-trans-propene hydrochloride (1) 1-(3-Cyanophenyl)piperazine By using 4.41 g of 3-cyanoaniline, the reaction and the post treatment of Example 30 (1) were repeated to thereby give 2.62 g of title compound in the form of a yellow oily product.

1H-NMR (CDCl$_3$): 3.03 (t, 2H, J=5 Hz), 3.18 (t, 2H, J=5 Hz), 7.0–7.2 (m, 3H), 7.32 (dd, 1H, J=7, 9 Hz).

(2) 1-[5-Methyl-1-(2-pyrimidinyl)-4-pyrazolyl]-3-[4-(3-cyanophenyl)-1-piperazinyl]-1-propanone hydrochloride By using 500 mg of the compound obtained in the above (1), the reaction and the post treatment of Example 30 (2) were repeated to thereby give 419 mg of title compound in the form of a colorless solid product.

$^1$H-NMR (DMSO-d$_6$): 2.82 (s, 3H), 3.1–3.3 (m, 4H), 3.4–3.6 (m, 4H), 3.6–3.7 (m, 2H), 3.9–4.0 (m, 2H), 7.26 (d, 1H, J=8 Hz), 7.37 (dd, 1H, J=8, 2 Hz), 7.45 (t, 1H, J=8 Hz), 7.47 (d, 1H, J=2 Hz), 7.66 (t, 1H, J=5 Hz), 8.43 (s, 1H), 9.01 (d, 2H, J=5 Hz).

(3) 1-[5-Methyl-1-(2-pyrimidinyl)-4-pyrazolyl]-3-[4-3-cyanophenyl)-1-piperazinyl]-1-trans-propene hydrochloride By using 350 mg of the compound obtained in the above (2), the reaction and the post treatment of Example 30 (3) were repeated to thereby give 165 mg of title compound in the form of colorless crystals.

m.p.: 215°–225° C. (decomp.); $^1$H-NMR (DMSO-$d_6$): 2.62 (s, 3H), 3.0–3.3 (m, 4H), 3.5–3.6 (m, 2H), 3.9–4.1 (m, 4H), 6.23 (dt, 1H, J=16, 8 Hz), 6.82 (d, 1H, J=16 Hz), 7.25 (d, 1H, J=7 Hz), 7.39 (d, 1H, J=8 Hz), 7.4–7.5 (m, 2H), 7.54 (t, 1H, J=5 Hz), 8.08 (s, 1H), 8.92 (d, 2H, J=5 Hz).

Example 33

1-[5-Methyl-1-(2-pyrimidinyl)-4-pyrazolyl]-3-[4-(3-carbamoylphenyl)-1-piperazinyl]-1-trans-propene hydrochloride 88 mg of the compound obtained in Example 32 (3) was dissolved in 0.5 ml of conc. hydrochloric acid and stirred at room temperature for 62 hours. Then the reaction mixture was neutralized with a saturated aqueous solution of sodium hydrogencarbonate and extracted with chloroform. The extract was washed with a saturated aqueous solution of sodium chloride and dried over anhydrous sodium sulfate. After evaporating the solvent, the residue was purified by silica gel column chromatography (chloroform:methanol=100:3). Then the product was converted into hydrochloride with a 1N hydrochloric acid/ethanol solution and recrystallized from ethanol. Thus 50 mg of the title compound was obtained in the form of colorless crystals.

m.p.: 140°–146° C. (decomp.); $^1$H-NNR (DMSO-$d_6$): 2.63 (s, 3H), 3.1–3.3 (m, 4H), 3.5–3.7 (m, 2H), 3.8–4.0 (m, 4H), 6.24 (dt, 1H, J=16, 8 Hz), 6.84 (d, 1H, J=16 Hz), 7.16 (d, 1H, J=8 Hz), 7.33 (t, 1H, J=8 Hz), 7.38 (d, 1H, J=8 Hz), 7.48 (brs, 1H), 7.53 (t, 1H, J=5 Hz), 8.08 (s, 1H), 8.92 (d, 2H, J=5 Hz).

Example 34

1-[5-Methyl-1-(2-pyrimidinyl)-4-pyrazolyl]-3-[4-(5-chloro-2-hydroxyphenyl)-1-piperazinyl]-1-trans-propene hydrochloride (1) 1-(5-Chloro-2-hydroxyphenyl piperazine A solution of 3.0 g of 2-amino-4-chlorophenol and 3.73 g of bis(2-chloroethyl)amine hydrochloride in 1-butanol (35 ml) was heated under reflux for 24 hours. After adding 2.21 g of sodium carbonate, the mixture was heated under reflux for additional 12 hours. After allowing to cool, the insoluble matters were collected by filtration and suspended in an aqueous solution of sodium hydroxide. After washing with chloroform, it was neutralized with an aqueous solution of ammonium chloride and extracted with chloroform. The extract was washed with saturated aqueous solution of sodium chloride and dried over anhydrous sodium sulfate. After evaporating the solvent, 1.90 g of the title compound was obtained in the form of a brown solid product.

$^1$H-NMR (CDCl$_3$): 2.82 (t, 4H, J=5 Hz), 3.04 (t, 4H, J=5 Hz), 6.88 (d, 1H, J=9 Hz), 7.04 (dd, 1H, J=9, 2 Hz), 7.11 (d, 1H, J=2 Hz).

(2) 1-[5-Methyl-1-(2-pyrimidinyl)-4-pyrazolyl]-3-[4-(5-chloro-2-hydroxyphenyl)-1-piperazinyl]-1-propanone hydrochloride By using 400 mg of the compound obtained in the above (1), the reaction and the post treatment of Example 30 (2) were repeated to thereby give 294 mg of title compound.

$^1$H-NMR (DMSO-$d_6$): 2.82 (s, 3H), 2.9–3.1 (m, 2H), 3.2–3.4 (m, 2H), 3.4–3.7 (m,8H), 6.84 (d, 1H, J=8 Hz), 6.88 (brs, 1H), 6.89 (d, 1H, J=8 Hz), 7.66 (t, 1H, J=5 Hz), 8.42 (s, 1H), 9.01 (d, 2H, J 5 Hz).

(3) 1-[5-Methyl-1-(2-pyrimidinyl)-4-pyrazolyl]-3-[4-(5-chloro-2-hydroxyphenyl)-1-piperazinyl]-1-trans-propene hydrochloride 250 mg of the compound obtained in the above (2) was dissolved in a solvent mixture comprising 10 ml of ethanol and 10 ml of tetrahydrofuran, and stirred under ice-cooling for 1.5 hour. During this period, 90 mg of sodium boron hydride was added in portions. Then 1.5 ml of 10% hydrochloric acid was added and the solvent was removed by evaporation. To the residue were added 20 ml of tetrahydrofuran and 167 mg of p-toluenesulfonic acid monohydrate, and the obtained mixture was heated under reflux for 20 minutes. After evaporating the solvent, the residue was neutralized with an aqueous solution of sodium hydrogencarbonate and extracted with chloroform. The extract was successively washed with water and a saturated aqueous solution of sodium chloride, and dried over anhydrous sodium sulfate. After evaporating the solvent, the residue was purified by silica gel column chromatography (chloroform:methanol=100:1). Then the product was converted into hydrochloride with a 1N hydrochloric acid/ethanol solution and recrystallized from ethanol. Thus 131 mg of the title compound was obtained in the form of colorless crystals.

m.p.: 210°–220° C. (decomp.); $^1$H-NMR (DMSO-$d_6$): 2.63 (s, 3H), 2.9–3.1 (m, 2H), 3.1–3.3 (m, 2H), 3.5–3.7 (m, 4H), 3.9–4.0 (m, 2H), 6.23 (dt, 1H, J=16, 8 Hz), 6.8–7.0 (m, 4H), 7.54 (t, 1H, J=5 Hz), 8.09 (s, 1H), 8.92 (d, 2H, J=5 Hz).

Example 35

1-[5-Methyl-1-(2-pyrimidinyl)-4-pyrazolyl]-3-[4-(2-hydroxyphenyl)-1-piperazinyl]-1-trans-propene hydrochloride (1) 1-[5-Methyl-1-(2-pyrimidinyl)-4-pyrazolyl]-3-[4-(2-hydroxyphenyl)-1-piperazinyl]-1-propanone hydrochloride To 700 mg of 1-(2-hydroxyphenyl)piperazine dihydrobromide was added a saturated aqueous solution of sodium hydrogencarbonate. After extracting with chloroform, the extract was washed with a saturated aqueous solution of sodium chloride and dried over anhydrous sodium sulfate. After evaporating the solvent, 397 mg of 4-acetyl-1-(2-pyrimidinyl)-5-methylpyrazole, 3.0 ml of a 1N hydrochloric acid/ethanol solution and 40 ml of ethanol were added to the residue and the mixture was heated under reflux for 58 hours. During this period, 3.0 g of paraformaldehyde was added in portions. After cooling, the insoluble matters were collected by filtration to thereby give 176 mg of the title compound.

$^1$H-NMR (DMSO-$d_6$): 2.82 (s, 3H), 2.9–3.1 (m, 2H), 3.2–3.3 (m, 2H), 3.4–3.6 (m, 6H), 3.6–3.7 (m, 2H), 6.77 (t, 1H, J=7 Hz), 6.84 (d, 1H, J=7 Hz), 6.87 (t, 1H, J=7 Hz), 6.91 (d, 1H, J=7 Hz), 7.67 (t, 1H, J 5 Hz), 8.43 (s, 1H), 9.01 (d, 1H, J=5 Hz).

(2) 1-[5-Methyl-1-(2-pyrimidinyl)-4-pyrazolyl]-3-[4-(2-hydroxyphenyl)-1-piperazinyl]-1-trans-propene hydrochloride By using 158 mg of the compound obtained in the above (1), the reaction and the post treatment of Example 34 (3) were repeated to thereby give 72 mg of title compound in the form of colorless crystals.

m.p.: 216°–228° C. (decomp.); $^1$H-NMR (DMSO-$d_6$): 2.64 (s, 3H), 2.9–3.1 (m, 2H), 3.1–3.3 (m, 2H), 3.4–3.6 (m, 4H), 3.9–4.0 (m, 2H), 6.24 (dt, 1H, J=16, 8 Hz), 6.76 (t, 1H, J=8 Hz), 6.84 (d, 1H, J=16 Hz), 6.85 (d, 1H, J=8 Hz), 6.88 (t, 11H, J=8 Hz), 6.90 (d, 1H, J=8 Hz), 7.53 (t, 1H, J=5 Hz), 8.09 (s, 1H), 8.92 (d, 2H, J=5 Hz).

Example 36

1-[5-Methyl-1-(2-pyrimidinyl)-4-pyrazolyl]-3-[4-(4-methoxyphenyl)-1-piperazinyl]-1-trans-propene hydrochloride (1) 1-[5-Methyl-1-(2-pyrimidinyl)-4-pyrazolyl]-3-[4-(4-methoxyphenyl)-1-piperazinyl]-1-propanone hydrochloride 1.0 g of 1-(2-pyrimidinyl)-4-acetyl-5-methyl-pyrazole was dissolved in 50 ml of ethanol. After adding 1.3 g of 1-(4-methoxyphenyl)piperazine dihydrochloride and 0.8 g of paraformaldehyde, the mixture was heated under reflux for 24 hours. Further, 0.8 g of paraformaldehyde was added and the resulting mixture was heated under reflux for additional 48 hours. Then the reaction mixture was concentrated and neutralized by adding a saturated aqueous solution of sodium hydrogencarbonate. After extracting with chloroform, the extract was washed with a saturated aqueous solution of sodium chloride and dried over anhydrous sodium sulfate. After evaporating the solvent, the residue thus obtained was purified by silica gel column chromatography (chloroform:methanol=50:1), converted into hydrochloride by adding a 1N hydrochloric acid/ethanol solution and then recrystallized from ethanol. Thus 1.1 g of the title compound was obtained in the form of a pale yellow powder.

m.p.: 150.9°–152.8° C.; $^1$H-NMR (DMSO-d$_6$): 2.81 (s, 3H), 3.0–3.1 (m, 2H), 3.2–3.3 (m, 2H), 3.4–3.5 (m, 4H), 3.5–3.7 (m, 4H), 3.70 (s, 3H), 6.87 (d, 2H, J=9.3 Hz), 6.97 (d, 2H, J=9.3 Hz), 7.67 (t, 1H, J=4.9 Hz), 8.43 (s, 1H), 9.10 (d, 2H, J=4.9 Hz).

(2) 1-[5-Methyl-1-(2-pyrimidinyl)-4-pyrazolyl]-3-[4-(4-methoxyphenyl)-1-piperazinyl]-1-trans-propene hydrochloride 80 mg of the compound obtained in the above (1) was dissolved in a solvent mixture comprising 5 ml of ethanol and 5 ml of tetrahydrofuran. Then 16 mg of sodium boron hydride was added thereto at –10° C. and the mixture was stirred for 1 hour. The reaction was ceased by adding a 1N hydrochloric acid/ethanol solution and the solvent was removed by evaporation. The residue thus obtained was dissolved in a solvent mixture comprising 5 ml of 1,4-dioxane and 5 ml of tetrahydrofuran. After adding 38 mg of p-toluenesulfonic acid monohydrate, the mixture was heated under reflux for 1 hour. Next, the reaction mixture was concentrated, neutralized by adding a saturated aqueous solution of sodium hydrogencarbonate and then extracted with chloroform. The extract was washed with a saturated aqueous solution of sodium chloride and dried over anhydrous sodium sulfate. After evaporating the solvent, the obtained residue was purified by silica gel column chromatography (chloroform:methanol=50:1), converted into hydrochloride by adding a 1N hydrochloric acid/ethanol solution and then recrystallized from ethanol. Thus 31 mg of the title compound was obtained in the form of a white powder.

m.p.: 154.3°–155.5° C.; $^1$H-NMR (DMSO-d$_6$): 2.62 (s, 3H), 3.0–3.1 (m, 2H), 3.1–3.2 (m, 2H), 3.5–3.7 (m, 4H), 3.70 (s, 3H), 3.9–4.0 (m, 2H), 6.22 (dt, 1H, J=16.1, 7.3 Hz), 6.82 (d, 1H, J=16.1 Hz), 6.86 (d, 2H, J=9.0 Hz), 6.96 (d, 2H, J=9.0 Hz), 7.54 (t, 1H, J=4.9 Hz), 8.10 (s, 1H), 8.93 (d, 2H, J=4.9 Hz).

Example 37

1-[5-Methyl-1-(2-pyrimidinyl)-4-pyrazolyl]-3-[4-(4-hydroxyphenyl)-1-piperazinyl]-1-trans-propene hydrochloride (1) 1-[5-Methyl-1-(2-pyrimidinyl)-4-pyrazolyl]-3-[4-(4-hydroxyphenyl)-1-piperazinyl]-1-propanone hydrochloride 2.0 g of 1-(2-pyrimidinyl)-4-acetyl-5-methylpyrazole was dissolved in 50 ml of ethanol. After adding 2.6 g of 1-(4-hydroxyphenyl)piperazine, 10 ml of a 1N hydrochloric acid/ethanol solution and 1.6 g of paraformaldehyde, the mixture was heated under reflux for 24 hours. Further, 3.2 g of paraformaldehyde was added and the resulting mixture was heated under reflux for additional 48 hours. Then the reaction mixture was concentrated and neutralized by adding a saturated aqueous solution of sodium hydrogencarbonate. After extracting with chloroform, the extract was washed with a saturated aqueous solution of sodium chloride and dried over anhydrous sodium sulfate. After evaporating the solvent, the residue thus obtained was purified by silica gel column chromatography (chloroform:methanol=20:1), converted into hydrochloride by adding a 1N hydrochloric acid/ethanol solution and then recrystallized from ethanol. Thus 946 mg of the title compound was obtained in the form of a pale brown powder.

m.p.: 141.8°–142.9° C. (decomp.); $^1$H-NMR (DMSO-d$_6$): 2.90 (s, 3H), 3.08 (t, 2H, J=4.2 Hz), 3.1–3.2 (m, 2H), 3.4–3.5 (m, 2H), 3.5–3.8 (m, 4H), 6.68 (d, 2H, J=9.2 Hz), 6.8–6.9 (m, 2H), 7.55 (t, 1H, J=4.9 Hz), 8.04 (s, 1H), 8.93 (d, 2H, J=4.9 Hz).

(2) 1-[5-Methyl-1-(2-pyrimidinyl)-4-pyrazolyl]-3-[4-(4-hydroxyyhenyl)-1-piperazinyl]-1-trans-propene hydrochloride By using 437 mg of the compound obtained in the above (1), the reaction and the post treatment of Example 36 (2) were repeated to thereby give 337 mg of the title compound in the form of a pale brown powder.

m.p.: 136.2°–137.5° C. (decomp.); $^1$H-NMR (DMSO-d$_6$): 2.62 (s, 3H), 3.0–3.1 (m, 2H), 3.1–3.2 (m, 2H), 3.5–3.7 (m, 4H), 3.9–4.0 (m, 2H), 6.23 (dt, 1H, J=16.3, 6.5 Hz), 6.74 (d, 2H, J=8.3 Hz), 6.87 (d, 1H, J=16.3 Hz), 6.91 (d, 2H, J=8.3 Hz), 7.58 (t, 1H, J=4.8 Hz), 8.13 (s, 1H), 8.93 (d, 2H, J=4.8 Hz).

Example 38

1-[5-Methyl-1-(2-pyrimidinyl)-4-pyrazolyl]-3-[4-diphenylmethyl-1-piperazinyl]-1-trans-propene dihydrochloride (1) 1-[5-Methyl-1-(2-pyrimidinyl)-4-pyrazolyl]-3-[4-diphenylmethyl-1-piperazinyl]-1-propanone hydrochloride By using 1.26 g of 1-(diphenylmethyl)piperazine, the reaction and the post treatment of Example 36 (1) were repeated to thereby give 867 mg of the-title compound.

m.p.: 220°–223° C. (decomp.); $^1$H-NMR (DMSO-d$_6$): 2.80 (s, 3H), 3.1–3.6 (m, 12H), 4.49 (s, 1H), 7.2–7.5 (m, 10H), 7.66 (t, 1H, J=5 Hz), 8.38 (s, 1H), 9.00 (d, 2H, J=5 Hz).

(2) 1-[5-Methyl-1-(2-pyrimidinyl)-4-pyrazolyl]-3-[4-diphenylmethyl-1-piperazinyl]-1-trans-propene dihydrochloride 806 mg of the compound obtained in the above (1) was dissolved in a solvent mixture comprising 35 ml of anhydrous ethanol and 35 ml of anhydrous tetrahydrofuran. After ice-cooling to 0° C., 250 mg of sodium boron hydride was added thereto and the mixture was stirred at the same temperature for 1 hour. 50 mg of sodium boron hydride was further added and the mixture was stirred for additional 1 hour. Then the reaction mixture was neutralized by adding a 1N hydrochloric acid/ethanol solution. After evaporating the solvent, the residue thus concentrated was extracted with chloroform and a saturated aqueous solution of sodium hydrogencarbonate. The extract was washed with a saturated aqueous solution of sodium chloride and dried over anhydrous sodium sulfate. After evaporating the solvent, 25 ml of anhydrous dioxane, 25 ml of anhydrous tetrahydrofuran and 432 mg of p-toluenesulfonic acid monohydrate were added to the residue and the resulting mixture was heated under reflux for 5 hours. After evaporating the solvent, the residue was extracted with chloroform and a saturated aqueous solution of sodium hydrogencarbonate. The extract was washed with a saturated aqueous solution of sodium chloride and dried over anhydrous sodium sulfate. After evaporating the solvent, the obtained residue was purified by silica gel column chromatography (40 g, chloroform:methanol=50:1), converted into hydrochloride by adding a 1N hydrochloric acid/ethanol solution and then recrystallized from ethanol. Thus 128 mg of the title compound was obtained.

m.p.: 202°–205° C.; $^1$H-NMR (DMSO-$d_6$): 2.60 (s, 3H), 3.4–3.8 (m, 10H), 4.38 (s, 1H), 6.15 (dt, 1H, J=16, 8 Hz), 6.82 (d, 1H, J=16 Hz), 7.1–7.4 (m, 10H), 7.53 (t, 1H, J=5 Hz), 8.04 (s, 1H), 8.91 (d, 2H, J=5 Hz).

Example 39

1-[5-Methyl-1-(2-pyrimidinyl)-4-pyrazolyl]-3-[4-benzyl-1-piperazinyl]-1-trans-propene dihydrochloride (1) 1-[5-Methyl-1-(2-pyrimidinyl)-4-pyrazolyl]-3-[4-benzyl-1-piperazinyl]-1-propanone hydrochloride 1.01 g of 4-acetyl-1-(2-pyrimidinyl)-5-methylpyrazole was dissolved in 80 ml of anhydrous ethanol. After adding 1.25 g of 1-benzylpiperazine hydrochloride and 0.45 g of paraformaldehyde, the mixture was heated under reflux for 18 hours. Further, 0.60 g of 1-benzylpiperazine hydrochloride and 0.20 g of paraformaldehyde were added and the resulting mixture was heated under reflux for additional 8 hours. After cooling, the crystals were collected by filtration and extracted with chloroform and a saturated aqueous solution of sodium hydrogencarbonate. The extract was washed with a saturated aqueous solution of sodium chloride and dried over anhydrous sodium sulfate. After evaporating the solvent, the residue thus obtained was purified by silica gel column chromatography (50 g, chloroform:methanol= 50:1), converted into hydrochloride by adding a 1N hydrochloric acid/ethanol solution and then recrystallized from ethanol. Thus 742 mg of the title compound was obtained.

m.p.: 166°–169° C. (decomp.); $^1$H-NMR (DMSO-$d_6$): 2.80 (s, 3H), 3.2–3.8 (m, 14H), 7.4–7.7 hI (m, 5H), 7.66 (t, 1H, J=5 Hz), 8.36 (s, 1H), 9.00 (d, 2H, J=5 Hz).

(2) 1-[5-Methyl-1-(2-pyrimidinyl)-4-pyrazolyl]-3-[4-benzyl-1-piperazinyl]-1-trans-propene dihydrochloride By using 430 mg of the compound obtained in the above (1), the reaction and the post treatment of Example 38 (2) were repeated to thereby give 132 mg of the title compound.

m.p.: 197°–201° C. (decomp.); $^1$H-NMR (DMSO-$d_6$): 2.62 (s, 3H), 3.2–4.0 (m, 12H), 6.15 (dt, 1H, J=16, 8 Hz), 6.85 (d, 1H, J=16 Hz), 7.4–7.4 (m, 5H), 7.53 (t, 1H, J=5 Hz), 8.03 (s, 1H,), 8.91 (d, 2H, J=5 Hz).

Example 40

1-[5-Methyl-1-(2-pyrimidinyl)-4-pyrazolyl]-3-[4-piperidino-1-piperidyl]-1-trans-propene dihydrochloride (1) 1-[5-Methyl-1-(2-pyrimidinyl)-4-pyrazolyl]-3-[4-piperidino-1-piperidyl]-1-propanone dihydrochloride By using 1.23 g of 4-piperidinopiperidine, the reaction and the post treatment of Example 39 (1) were repeated to thereby give 900 mg of the title compound.

m.p.: 274°–278° C. (decomp.); $^1$H-NMR (CD$_3$OD): 1.8–2.1 (m, 4H), 2.15–2.3 (m, 2H), 2.4–2.5 (m, 2H), 2.98 (s, 3H), 3.0–3.1 (m, 1H), 3.15–3.35 (m, 4H), 3.45–3.65 (m, 6H), 3.8–3.9 (m, 2H), 7.55 (t, 1H, J=5 Hz), 8.35 (s, 1H), 8.93 (d, 2H, J=5 Hz).

(2) 1-[5-Methyl-1-(2-pyrimidinyl)-4-pyrazolyl]-3-[4-piperidino-1-piperidyl]-1-trans-propene dihydrochloride By using 420 mg of the compound obtained in the above (1), the reaction and the post treatment of Example 38 (2) were repeated to thereby give 98 mg of the title compound.

m.p.: 267°–273° C. (decomp.); $^1$H-NMR (CD$_3$OD): 1.8–2.0 (m, 4H), 2.05–2.1 (m, 2H), 2.4–2.5 (m, 2H), 2.74 (s, 3H), 3.0–3.2 (m, 2H), 3.25–3.4 (m, 6H), 3.5–3.6 (m, 2H), 3.7–3.8 (m, 1H), 3.9–4.0 (m, 2H), 6.21 (dt, 1H, J=16, 8 Hz), 6.90 (d, 1H, J=16 Hz), 7.45 (t, 1H, J=5 Hz), 8.07 (s, 1H), 8.86 (d, 2H, J=5 Hz).

Example 41

1-[5-Methyl-1-(2-pyrimidinyl)-4-pyrazolyl]-3-[4-(2,5-difluorophenyl)-1-piperazinyl]-1-trans-propene hydrochloride (1) 1-(2,5-Difluorophenyl)piperazine hydrochloride 7.0 g of bis(2-chloroethyl)amine hydrochloride was suspended in 60 ml of butanol and 5 g of 2,5-difluoroaniline was added thereto at room temperature. After heating under reflux for 72 hours, the reaction mixture was cooled and 4.1 g of sodium carbonate was added. After heating under reflux for additional 24 hours, the precipitate was taken up by filtration, dissolved in water and extracted with chloroform. Then the extract was washed successively with water and a saturated aqueous solution of sodium chloride, and dried over anhydrous sodium sulfate. After evaporating the solvent, the residue was dissolved in a small amount of chloroform, converted into hydrochloride by adding a 4N hydrochloric acid/dioxane solution and filtered to thereby give 2.39 g mg of the title compound.

m.p.: 185°–190° C. (decomp.); $^1$H-NMR (CD$_3$OD): 3.25–3.45 (m, 8H), 6.76 (ddd, 1H, J 12, 8, 3 Hz), 6.86 (ddd, 1H, J=10, 7, 3 Hz), 7.09 (ddd, 1H, J=12, 9, 5 Hz).

(2) 1-[5-Methyl-1-(2-pyrimidinyl)-4-pyrazolyl]-3-[4-(2,5-difluorophenyl)-1-piperazinyl]-1-propanone hydrochloride By using 1.00 g of 1-(2,5-difluorophenyl)piperazine hydrochloride, the reaction and the post treatment of Example 36 (1) were repeated to thereby give 190 mg of the title compound.

m.p.: 174°–176° C. (decomp.); $^1$H-NMR-(DMSO-$d_6$): 2.82 (s, 3H), 3.1–3.2 (m, 2H), 3.2–3.4 (m, 4H), 3.5–3.7 (m, 6H), 6.8–6.9 (m, 1H), 6.95–7.05 (m, 1H), 7.2–7.3 (m, 1H), 7.67 (t, 1H, J=5 Hz), 8.42 (s, 1H), 9.00 (d, 2H, J=5 Hz).

(3) 1-[5-Methyl-1-(2-pyrimidinyl)-4-pyrazolyl]-3-[4-(2,5-difluorophenyl)-1-piperazinyl]-1-trans-propene hydrochloride By using 165 mg of the compound obtained in the above (2), the reaction and the post treatment of Example 38 (2) were repeated to thereby give 54 mg of the title compound.

m.p.: 209°–212° C. (decomp.); $^1$H-NMR (DMSO-$d_6$): 2.63 (s, 3H), 3.1–3.3 (m, 4H), 3.5–3.65 (m, 4H), 3.9–4.0 (m, 2H), 6.22 (dt, 1H, J=16, 8 Hz), 6.82 (d, 1H, J=16 Hz), 6.8–6.9 (m, 1H), 7.00 (ddd, 1H, J=10, 7, 3 Hz), 7.22 (ddd, 1H, J=12, 9, 5 Hz), 7.54 (t, 1H, J=5 Hz), 8.09 (s, 1H), 8.92 (d, 1H, J=5 Hz).

Example 42

1-[5-Methyl-1-(2-pyrimidinyl)-4-pyrazolyl]-3-[4-(2,5-dichlorophenyl)-1-piperazinyl]-1-trans-propene hydrochloride (1) 1-(2,5-Dichlorophenyl)piperazine hydrochloride 7.14 g of bis(2-chloroethyl)amine hydrochloride was suspended in 70 ml of butanol and 6.48 g of 2,5-dichloroaniline was added thereto at room temperature. After heating under reflux for 48 hours, the reaction mixture was cooled and 5.52 g of potassium carbonate was added. After heating under reflux for additional 24 hours, the insoluble matters were filtered off and the filtrate was concentrated. Then the obtained residue was extracted with chloroform and a saturated aqueous solution of sodium hydrogencarbonate. The extract was washed with water and a saturated aqueous solution of sodium chloride, and dried over anhydrous sodium sulfate. After evaporating the solvent, the residue was purified by silica gel column chromatography (100 g, chloroform:methanol=50:1–30:1). The product was converted into hydrochloride by adding a 1N hydrochloric acid/ethanol solution to thereby give 1.41 g of the title compound.

m.p.: 200°–205° C. (decomp.); $^1$H-NMR (CD$_3$OD): 3.25–3.45 (m, 8H), 7.13 (d, 1H, J=8 Hz), 7.20 (s, 1H), 7.40 (d, 1H J=8 Hz).

(2) 1-[5-Methyl-1-(2-pyrimidinyl)-4-pyrazolyl]-3-[4-(2,5-dichlorophenyl)-1-piperazinyl]-1-propanone hydrochloride By using 1.40 g of 1-(2,5-dichlorophenyl)piperazine hydrochloride, the reaction and the post treatment of Example 36 (1) were repeated to thereby give 595 mg of the title compound.

m.p.: 200°–203° C. (decomp.); $^1$H-NMR (DMSO-d$_6$): 2.82 (s, 3H), 3.1–3.3 (m, 4H), 3.45–3.6 (m, 6H), 3.65–3.75 (m, 4H), 7.18 (d, 2H, J=8 Hz), 7.27 (s, 1H), 7.49 (d, 1H, J=8 Hz), 7.66 (t, 1H, J=5 Hz), 8.42 (s, 1H), 9.00 (d, 2H, J=5 Hz).

(3) 1-[5-Methyl-1-(2-pyrimidinyl)-4-pyrazolyl]-3-[4-(2,5-dichlorophenyl)-1-piperazinyl]-1-trans-propene hydrochloride By using 564 mg of the compound obtained in the above (2), the reaction and the post treatment of example 38 (2) were repeated to thereby give 378 mg of the title compound.

m.p.: 210°–215° C. (decomp.); $^1$H-NMR (DMSO-d$_6$): 2.63 (s, 3H), 3.1–3.3 (m, 4H), 3.4–3.7 (m, 4H), 3.95–4.05 (m, 2H), 6.22 (dt, 1H, J=16, 8 Hz), 6.83 (d, 1H, J=16 Hz), 7.18 (d, 2H, J=8 Hz), 7.27 (s, 1H), 7.49 (d, 1H, J=8 Hz), 7.54 (t, 1H, J=5 Hz), 8.10 (s, 1H), 8.92 (d, 2H, J=5 Hz).

INDUSTRIAL APPLICABILITY

Because of having antitumor effects, the compounds of the present invention represented by the formula (I) and salt thereof are useful as antitumor agents.

We claim:

1. A compound represented by the following formula (I) or its salt:

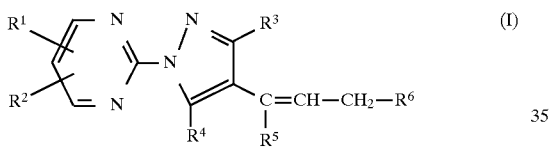

wherein $R^1$ and $R^2$ may be either the same or different and each represents an atom or a substituent selected from the group consisting of:
   (1) a hydrogen atom,
   (2) a halogen atom,
   (3) an amino group,
   (4) an alkylamino group,
   (5) a dialkylamino group,
   (6) a hydroxyl group,
   (7) a thiol group,
   (8) an alkylthio group,
   (9) an alkoxyl group,
   (10) a cyano group,
   (11) a carbamoyl group,
   (12) an alkyl group optionally-substituted by a halogen atom, an amino group, an alkylamino group, a dialkylamino group, a hydroxyl group, an alkoxyl group or a thiol group, and
   (13) an alkenyl group optionally substituted by a halogen atom, an amino group, an alkylamino group, a dialkylamino group, a hydroxyl group, an alkoxyl group or a thiol group;

$R^3$ represents a hydrogen atom or an alkyl group;
$R^4$ represents a hydrogen atom, an alkyl group, a phenyl group or a benzyl group;
$R^5$ represents a hydrogen atom or an alkyl group; and
$R^6$ represents a tetrahydroisoquinolyl group,
   a morpholinyl group,
   a piperidyl group,
   a piperazinyl group,

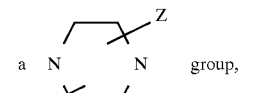

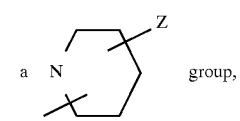

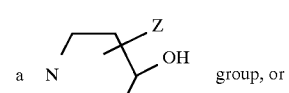

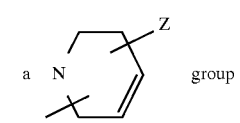

wherein Z represents a phenyl group,
   a pyridyl group,
   a pyrimidinyl group,
   a pyrazinyl group,
   a pyridazinyl group,
   a piperidyl group,
   a benzyl group,
   a benzhydryl group,

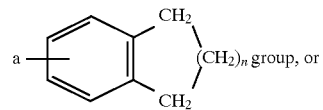

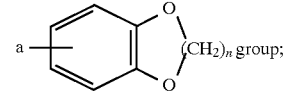

and
n represents an integer of from 1 to 3;
and $R^6$ is optionally substituted by one or more atom(s) and/or substituent(s) selected from a group consisting of:
   a halogen atom,
   an amino group,
   an alkylamino group,
   a dialkylamino group,
   an acetylamino group,
   a nitro group,
   a hydroxyl group,
   a thiol group,
   an alkylthio group,
   an alkoxyl group,
   a cyano group,
   a carbamoyl group,
   an alkyl group optionally substituted by a halogen atom, an amino group, an alkylamino group, a dialkylamino group, a hydroxyl group, an alkoxyl group or a thiol group, and
   an alkenyl group optionally substituted by a halogen atom, an amino group, an alkylamino group, a dialkylamino group, a hydroxyl group, an alkoxyl group or a thiol group.

2. A compound as claimed in claim 1 or its salt, wherein $R^3$ is a hydrogen atom and $R^4$ is a methyl group.

3. A compound as claimed in claim 1 or its salt, wherein $R^1$ and $R^2$ are atoms or substituents selected from a group consisting of:
- an alkyl group optionally substituted by a halogen atom, an amino group, a hydroxyl group, an alkoxyl group or a thiol group,
- a hydrogen atom,
- a halogen atom,
- an alkylamino group,
- a dialkylamino group,
- an alkoxyl group,
- a cyano group, and
- a carbamoyl group.

4. A compound as claimed in claim 1 or its salt, wherein $R^1$ and $R^2$ are atoms or substituents selected from the group consisting of:
- an alkyl group optionally substituted by a halogen atom, an amino group, a hydroxyl group, an alkoxyl group or a thiol group,
- a hydrogen atom,
- a halogen atom, and
- an alkoxyl group.

5. A compound as claimed in claim 1 or its salt, wherein $R^6$ represents

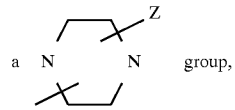

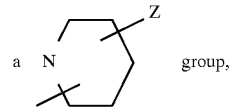

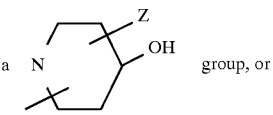

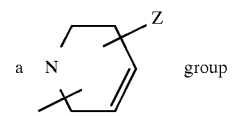

wherein Z is as defined in claim 1.

6. A compound as claimed in claim 1 or its salt, wherein $R^6$ represents

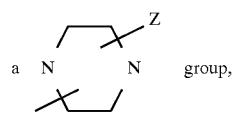

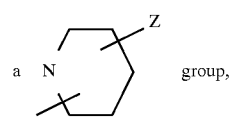

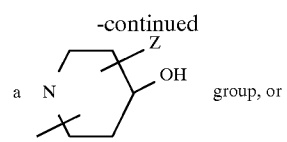

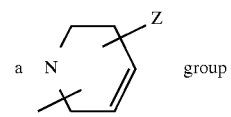

wherein Z is as defined in claim 1; each optionally substituted by one or more substituents selected from a group consisting of:
- an alkyl group optionally substituted by a halogen atom, an amino group, a hydroxyl group, an alkoxyl group or a thiol group,
- a halogen atom,
- an alkylamino group,
- a dialkylamino group,
- an alkoxyl group,
- a cyano group,
- a hydroxyl group, and
- a carbamoyl group.

7. A compound as claimed in claim 1 or its salt, wherein $R^6$ represents

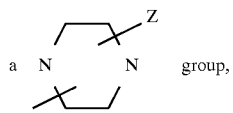

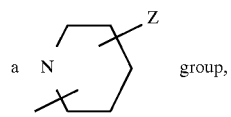

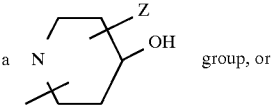

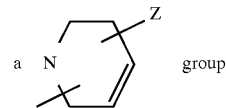

wherein Z is as defined in claim 1; each optionally substituted by one or more substituents selected from a group consisting of:
- an alkyl group optionally substituted by a halogen atom, an amino group, or a hydroxyl group,
- a halogen atom,
- an alkoxyl group, and
- a hydroxyl group.

8. A compound as claimed in claim 1 or its salt, wherein $R^6$ represents a group of the formula:

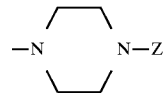

wherein Z is as defined in claim 1.

9. A compound as claimed in any of claims 5 to 8 or its salt, wherein Z is a phenyl group.

10. A compound as claimed in claim 1 or its salt, wherein $R^6$ is a group of the formula:
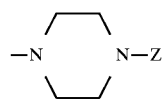
and Z is a phenyl group.
11. An antitumor agent which contains a compound as claimed in any of claims 1 to 10 or its salt as an active ingredient.
* * * * *